(12) United States Patent
Misawa et al.

(10) Patent No.: US 7,709,810 B2
(45) Date of Patent: May 4, 2010

(54) SENSING DEVICE, SENSING APPARATUS, AND SENSING METHOD

(75) Inventors: Hiroaki Misawa, Sapporo (JP); Kosei Ueno, Sapporo (JP); Yasuyuki Tsuboi, Sapporo (JP); Keiji Sasaki, Sapporo (JP)

(73) Assignee: National University Corporation Hokkaido University, Sapporo-shi (JP)

( * ) Notice: Subject to any disclaimer, the term of this patent is extended or adjusted under 35 U.S.C. 154(b) by 216 days.

(21) Appl. No.: 11/886,641

(22) PCT Filed: Mar. 17, 2006

(86) PCT No.: PCT/JP2006/305447

§ 371 (c)(1),
(2), (4) Date: Sep. 18, 2007

(87) PCT Pub. No.: WO2006/098446

PCT Pub. Date: Sep. 21, 2006

(65) Prior Publication Data

US 2009/0032735 A1 Feb. 5, 2009

(30) Foreign Application Priority Data

Mar. 18, 2005 (JP) ............................. 2005-080579

(51) Int. Cl.
*G21H 3/02* (2006.01)
*G01N 21/62* (2006.01)
(52) U.S. Cl. ................. 250/458.1; 356/301; 250/484.2; 250/483.1; 977/773; 977/774; 977/778; 977/779
(58) Field of Classification Search ....................... None
See application file for complete search history.

(56) References Cited

U.S. PATENT DOCUMENTS

| 2003/0228682 A1* | 12/2003 | Lakowicz et al. ........ 435/287.2 |
| 2006/0034729 A1* | 2/2006 | Poponin .................. 422/82.05 |
| 2008/0266555 A1* | 10/2008 | Murphy et al. ............ 356/301 |

FOREIGN PATENT DOCUMENTS

JP 2001-021565 1/2001

OTHER PUBLICATIONS

Gotschy et al., "Thin Films by Regular Patterns of Metal Nanoparticles: Tailoring the Optical Properties by Nanodesign." *Appl. Phys. B.*, v.63, pp. 381-384, 1996.

(Continued)

*Primary Examiner*—David P Porta
*Assistant Examiner*—Yara B Green
(74) *Attorney, Agent, or Firm*—The Nath Law Group; Jerald L. Meyer; Stanley N. Protigal

(57) ABSTRACT

There are provided a sensing device, a sensing apparatus, and a sensing method capable of realizing effective multi-photon absorption and local plasmon enhancement function. The sensing device can realize a high multi-photon excitation efficiency and selectivity by accurately controlling the material, shape, size, interval, and direction of metal particles arranged on a substrate. By employing the sensing device in various sensing apparatuses such as a fluorescent sensing apparatus, it is possible to realize sensing of detection object material with a high sensibility.

8 Claims, 14 Drawing Sheets

OTHER PUBLICATIONS

Craighead and Niklasson, "Characterization and Optical Properties of Arrays of Small Gold Particles." *Appl. Phys. Lett.*, v.44:12, pp. 1134-1135, 1984.

Masuda et al., "Long-Range-Ordered Anodic Porous Alumina with Less-Than-30 nm Hole Interval." *Japanese J. of Appl. Phys.*, v.45:43, pp. L1165-L1167, 2006.

* cited by examiner

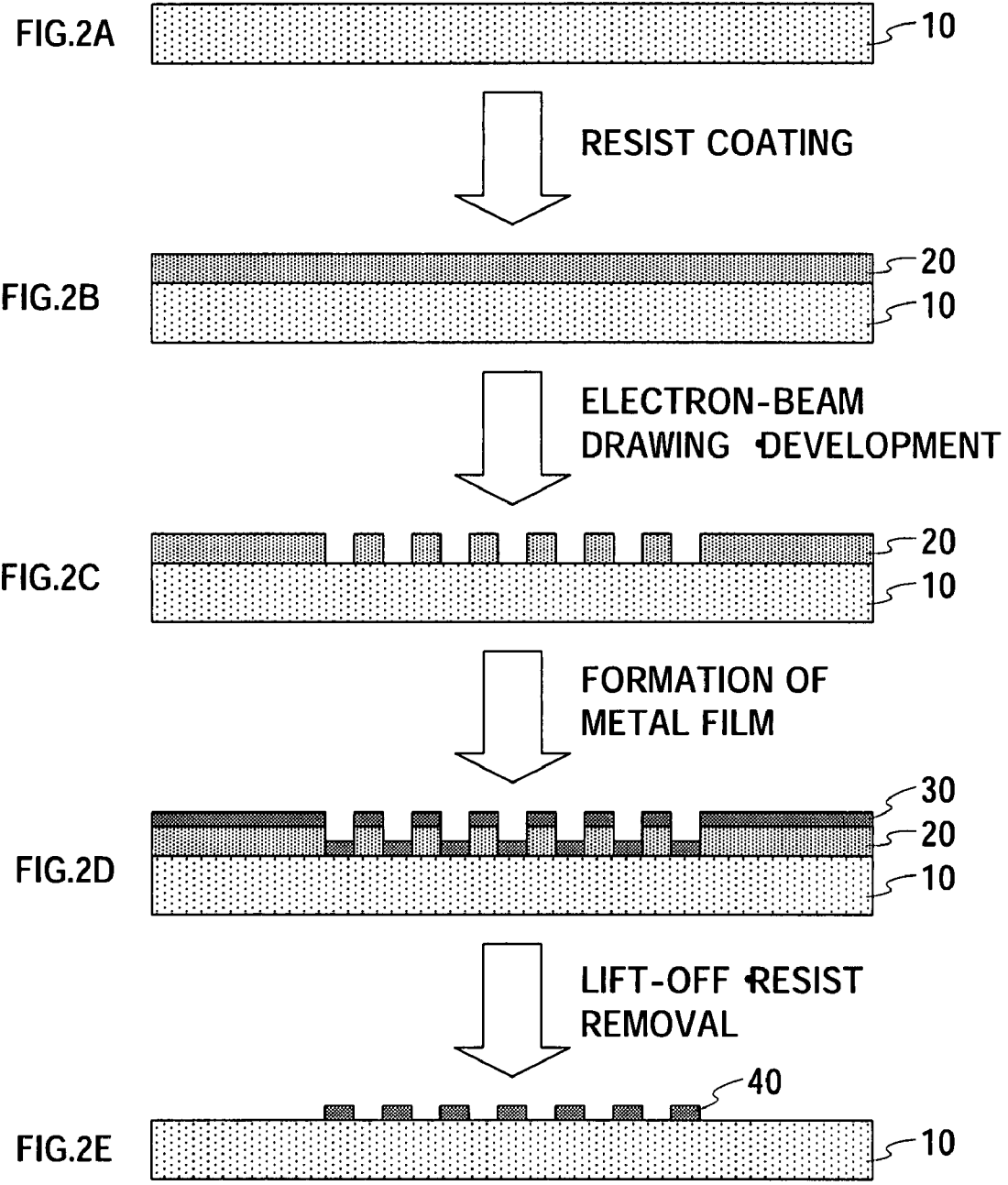

(240+x) nm 120 nm

SENSING DEVICE, SENSING APPARATUS, AND SENSING METHOD

TECHNICAL FIELD

The present invention relates to a sensing device, sensing apparatus and sensing method. More particularly, the present invention relates to a sensing device, sensing apparatus and sensing method for enhancing optical response from various kinds of sensing-target objects by surface (localized) plasmon and performing highly sensitive optical detection.

BACKGROUND ART

Fine metals (including, for example, fine metals having surface structures of the scale of nanometers and fine metal particles of the size of nanometers) exhibit a characteristic optical response (optical absorption), called "localized (surface) plasmon resonance absorption," in a specific wavelength range, according to their shape and size. Examples of metals exhibiting localized plasmon resonance absorption include precious metals such as gold, silver and platinum, and it is important that the plasmon resonance absorption wavelength changes according to the size and shape even for the same kind of metal. Utilizing this feature, applications of fine metals and fine metal particles such as described above to various kinds of optical devices (for example, optical filters) are anticipated.

Further, there are important applications of localized plasmon resonance absorption. The intensity of optical response (including, for example, fluorescence and light scattering (Raman scattering)) of molecules adsorbed to the metal exhibiting plasmon resonance is enhanced significantly by interactions between the molecules and surface plasmon. In other words, a metal structure, which is prepared by forming a metal that exhibits plasmon resonance on a substrate, functions as a high sensitivity sensing device for molecules, and application, research and development in this field are studied actively.

Raman scattering light is usually a weak optical response and should be enhanced efficiently to be used as a response signal of a sensor. Therefore, it has been difficult to use Raman scattering light as a response signal of a sensor even by enhancing with plasmon.

On the other hand, fluorescence is an optical response that can be obtained when the sensing-target object is fluorescent molecules or fluorescent-labeled molecules, and usually provides a stronger signal than scattering light such as in Raman scattering. Accordingly, fluorescence is suitable to be used as a response signal of a sensor by enhancement by plasmon resonance. It is therefore possible to detect fluorescent molecule or fluorescent-labeled molecule adsorbed to a metal structure exhibiting plasmon resonance absorption, with the help of fluorescence as a response signal. However, fluorescence (exciting light) from such fluorescent molecule adsorbed to a metal structure is quenched by energy transfer from the fluorescent molecule to fine metal (fine metal particle) adhered with the fluorescent molecule or the like even by being enhancing with plasmon, and is often difficult to use as a response signal.

Further, in fluorescent sensing, there are cases where an impurity (interfering substance) in the target system is excited by the excitation light for exciting the sensing-target substance. When the excited impurity is a fluorescent substance, the fluorescence from the interfering substance becomes an intense background signal (background light) and significantly degrades the sensing sensitivity and sensing precision for the sensing-target substance. Important examples of application of fluorescent sensing include biological analysis such as immunoassay analysis and gene (DNA) analysis, and, in such biological analysis, particularly, the fluorescence from the interfering substance (including serum and enzyme) becomes background light, resulting in a serious problem of causing deterioration of analysis precision.

To avoid the above problem of background light, a sensing method using two-photon excitation is proposed. Two-photon excitation refers to the phenomenon where an electronic excited state (i.e. fluorescent state) is induced by irradiating a light to sample, wherein the light has a wavelength twice the light wavelength (i.e. energy per photon is half) which can induce electronic transition of a fluorescent labeling reagent or fluorescent substance and making one molecule absorb two photons. By irradiating this two-photon excitation to a surface plasmon enhancing sensor, only a portion where the electric field of the excitation light is strongly localized by resonance plasmon is selectively excited. Therefore, it is possible to significantly reduce the influence of background light caused by interfering substance such as described above, and significantly improve sensing sensitivity and sensing precision.

As a technique to detects optical response using two-photon excitation, for example, there is the technique described in Patent Document 1.

Patent Document 1 discloses a fluorescent immunoassay analysis technique for supplying a sample solution containing an antigen to a thin metal film with an antibody fixed thereto so as to bond the antigen and antibody, supplying a fluorescence labeling reagent containing a fluorescent labeling antibody so as to bond the fluorescent labeling antibody to the antibody bonded to the antigen, irradiating light with a wavelength of an integral multiple of the wavelength of light that the fluorescent labeling antibody ordinarily absorbs to a glass prism having the thin metal film, inducing two-photon excitation or multiphoton excitation, and analyzing the spectrum of emitted fluorescence.

Patent Document 1: Japanese Patent Application Laid-Open No. 2001-021565

DISCLOSURE OF INVENTION

Problems to be Solved by the Present Invention

Generally, the absorption probability (absorption cross-sectional area) of multiphoton transition including two-photon transition is extremely lower (by the order of several tens digits) than the absorption probability of ordinary one-photon transition. Accordingly, even with the localized plasmon enhancement effect, it is difficult to efficiently induce multiphoton excitation.

According to the technique described in Patent Document 1, multiphoton absorption is induced by combining a thin metal film and glass prism, but the excitation rate is not disclosed. Further, although combining multiphoton absorption and the localized plasmon enhancing effect is an excellent idea for highly sensitive optical detection, it is very difficult to actually improve the excitation rate in multiphoton excitation as described above. In other words, the approach that has been performed to implement multiphoton excitation and plasmon enhancing effect with high efficiency is limited in its effect to a certain level. This is based on the fact that the knowledge virtually lacks about optimal structures of a metal structure (specifically, fine metal particles exhibiting plasmon resonance absorption arranged on the metal structure) that is an element of sensing-target systems.

Therefore, it can be said that design guidelines hardly exist for optical response sensors corresponding to the wavelength of an excitation light source and sensing-target substance. For example, if it is possible to provide spectral sensitivity functions to an optical response sensor, great improvements in the sensitivity of sensing can be expected by selecting a wavelength of an excitation light source to use, but providing such functions has actually been difficult. Further, high sensitivity sensing has generally been difficult.

Moreover, as described previously, such a sensing technique has not been developed sufficiently for using Raman scattering that is an extremely weak optical response as a response signal.

The present invention is made in view of the aforementioned problems, and it is therefore an object of the present invention to provide a sensing device, sensing apparatus and sensing method capable of realizing efficient multiphoton absorption and localized plasmon enhancing effect and sensing an optical response with high sensitivity and high precision.

Means for Solving the Problem

The sensing device of the present invention exhibits plasmon resonance absorption and employs a configuration having on a substrate a plurality of fine metal particles having a uniform size and arranged in the fixed direction at regular intervals.

The sensing apparatus of the present invention employs a configuration having: a sensing device comprising on a substrate a plurality of fine metal particles having a uniform size and arranged in a fixed direction at regular intervals; an excitation light irradiating section that irradiates an excitation light that makes a sensing-target substance adsorbed to the sensing device emit fluorescence to the sensing device; and a fluorescence intensity measuring section that measures an intensity of the fluorescence of the sensing-target substance.

The sensing method of the present invention comprises the steps of: irradiating an excitation light that makes a sensing-target substance adsorbed to a sensing device emit fluorescence to the sensing device, wherein the sensing device comprises on a substrate a plurality of fine metal particles having a uniform size and arranged in a fixed direction at regular intervals; and measuring an intensity of the fluorescence of the sensing-target substance.

Advantageous Effect of the Present Invention

According to the present invention, it is possible to provide a sensing device capable of regulating a resonance plasmon absorption wavelength of incident light irradiated to a detection target system, by precisely controlling the structure of the fine metal particle formed on the substrate.

Further, according to the present invention, by using the sensing device, it is possible to enhance optical responses such as fluorescence by localized plasmon, optical scattering (Raman scattering), long-wavelength emission, sum frequency, difference frequency and the like, and by using these optical responses, and high sensitivity sensing is realized.

Furthermore, according to the present invention, by using the sensing device, in addition to enhancing optical response by localized plasmon, excitation efficiency of multiphoton absorption can be improved, and by using fluorescence by multiphoton absorption as an optical response, high sensitivity- and high precision-sensing is realized.

BRIEF DESCRIPTION OF DRAWINGS

FIG. 2 shows cross-sectional views of steps to explain the manufacturing method of FIG. 1.

BEST MODE FOR CARRYING OUT THE PRESENT INVENTION

Figure 1:
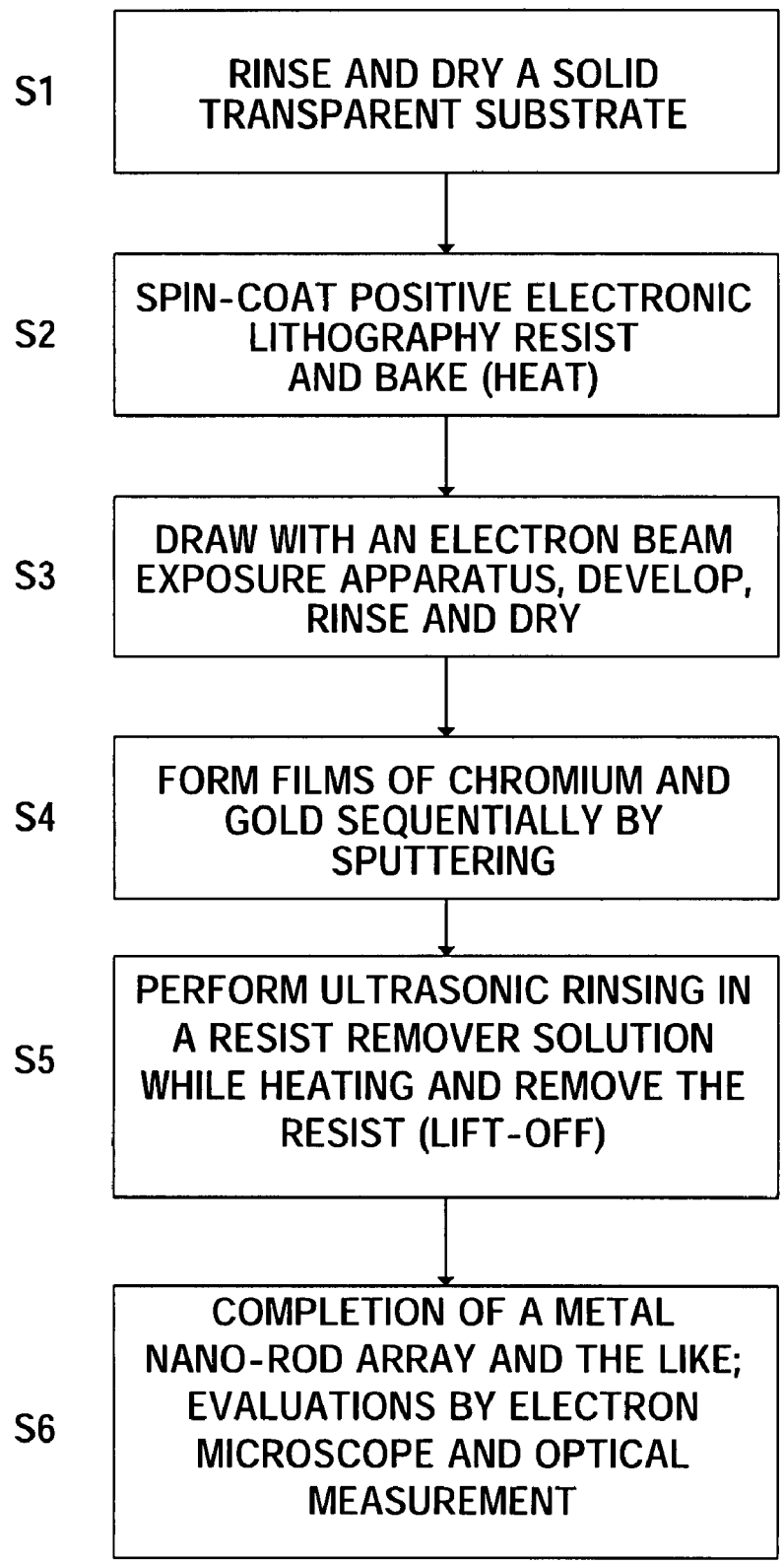
FIG. 1 is a flowchart illustrating a manufacturing method of a metal structure (sensing device) according to one embodiment of the present invention.

The present inventors have found out that it is necessary to unify the size and shape of each fine metal particle, the orientation of fine metal particle arrays, and the distance between fine metal particles, to improve plasmon enhancing effect, multiphoton excitation efficiency, and wavelength selectivity for incident light. Further, the present inventors have found out that in order to unify the size and shape of each fine metal particle, the orientation of fine metal particle arrays, and the distance between fine metal particles, semiconductor fine processing techniques can be applied, and the fine metal particles need to be precisely arranged regularly on a substrate.

Herein, the "wavelength selectivity" means sharpening an absorption maximum (peak) of the plasmon resonance absorption spectrum. By applying a metal structure having high wavelength selectivity to a sensing device, it is possible to sense a sensing-target substance with high sensitivity.

In the present invention the sensing-target substance can be adsorbed to a metal structure such that the number of fine metal particles (including, for example, metal nano-rod and metal nano-block) precisely controlled in size are integrated at regular tiny intervals in one axis direction on a solid substrate such as glass and the like, an optical response of light irradiated to the metal structure can be detected, and the metal structure can be used as a sensing device. It is thereby possible to realize a sensing apparatus both having excellent wavelength selectivity for incident light and high multiphoton excitation efficiency in plasmon resonance absorption properties. Further, the fluorescence (one-photon fluorescence, multi-photon fluorescence) of the molecular adsorbed to such a metal structure is not quenched by energy transfer into the metal, and enables high sensitivity sensing.

In other words, according to the present invention, by using a metal structure with fine metal particles precisely controlled in size and aligned at regular intervals as a sensing device, high sensitivity sensing is implemented based on enhancement of optical response by efficient multiphoton absorption and plasmon. Thus, the present invention relates to the method enabling to detect a sensing-target object by an optical response (preferably, multiphoton excitation fluorescence) from a molecule that is the sensing-target object adsorbed to the metal structure, by controlling the size and intervals of fine metal particles in the metal structure.

1. The Sensing Device of the Present Invention

Described next are features of the sensing apparatus of the present invention i.e. features of the metal structure used in the sensing device of the sensing apparatus. Particularly, the material, shape, size, intervals and direction of a plurality of fine metal particles formed on the substrate are specifically described.

(Materials of the Substrate)

Substrate on which a plurality of fine metal particles are arranged is not limited particularly. The substrate is preferably substrate formed of solid materials without optical absorption in the visible range to the IR range i.e. transparent substrate to use the metal structure as an optical response device. Specific examples of the substrate material include glass, quartz, sapphire and the like.

(Materials of Fine Metal Particles)

A feature of the fine metal particle arranged to align on the substrate is to exhibit plasmon resonance absorption. Examples of fine metal particle exhibiting plasmon resonance absorption include precious metals such as gold, silver, copper and platinum. Further, the fine metal particle may be particle obtained by plating other material with these precious metals.

(Shape of Fine Metal Particles)

The fine metal particle of the present invention have such a shape when the metal particle is cut into two parts, the two metal parts have same shape of cross section. For example, the fine metal particle of the present invention may have a shape of a hexahedron (cuboid) where all adjoining surfaces intersect with one another at right angles. In this case, when the fine metal particle is seen from an upper side perpendicular to the substrate, the fine metal particle seems to have a rectangular shape. In addition, each vertex of the rectangle does not need seem to be an exact right angle, and for example, each vertex may be in rounded-shape or in such a shape that edges of the vertex are cut. However, in this case, the vertexes of the rectangle preferably have the same shapes.

Further, each of the fine metal particles needs to be a fine metal particle exhibiting plasmon resonance absorption as described above, and the size (volume corresponding diameter) of the particle preferably ranges from 1 nm to 1000 nm, and, more preferably from 10 nm to 500 nm.

Furthermore, each fine metal particle has a shape having four vertexes with the same shape when seeing from the upper side perpendicular to the substrate. For example, in cuboid-shaped fine metal particle, vertexes of the rectangle correspond to four vertexes with the same shape. These four vertexes are adjoining to vertexes of four other fine metal particles respectively.

(Size of Fine Metal Particles)

It is a feature of each fine metal particle of the present invention to have a uniform size. The "uniform size" means that the area, volume and height of each fine metal particle arranged on the substrate are uniform. The "area of the fine metal particle" refers to the area of the fine metal particle seen from the upper side perpendicular to the substrate, and the "height of the fine metal particle" refers to the thickness of the fine metal particle from the surface of the substrate.

Herein, the "uniform area" means that the variability in the area of fine metal particles is 5% or less, and, more preferably, 2% or less. Further, the "uniform volume" means that the variability in the volume of fine metal particles is 5% or less, and, more preferably, 3% or less. The "uniform height" means that the variability in the height of fine metal particles is 10% or less, and preferably 5% or less.

As specific values, the area of each fine metal particle preferably ranges from about 100 $nm^2$ to 30,000 $nm^2$. The volume of the each metal particle preferably ranges from about 1000 $nm^3$ to 3,000,000 $nm^3$. The height (the thickness from the surface of the substrate) of each fine metal particle can be derived from the area and volume of each fine metal particle, and preferably ranges from 5 nm to 300 nm, and more preferably from 10 nm to 100 nm.

The area and volume of each fine metal particle seen from the upper side perpendicular to the substrate can be checked and calculated from electron microscope photographs of the fine metal particle. For example, when the fine metal particles are in the shape of a cuboid, the length of the long axis and the length of the short axis of the fine metal particle are read from the electron microscope photograph where the fine metal particle is seen from the upper side perpendicular to the substrate, and the area of the fine metal particle is calculated by multiplying the length of the long axis by the length of the short axis. Further, the height of the fine metal particle is read from the electron microscope photograph where the fine metal particle is seen from the lateral side parallel to the substrate, and the volume of the fine metal particle is calculated by multiplying the calculated area by the read height.

(Intervals of the Fine Metal Particles)

It is another feature of the fine metal particles of the present invention that the particles are arranged at regular intervals. "Regular intervals" means that the shortest distance between any one of a plurality of fine metal particles arranged on the substrate and an adjoining particle is 30 nm or less (more preferably, 10 nm or less), and that the variability in the interval is 5% or less.

As described above, since the four vertexes of each fine metal particle are adjoining to one vertex of other four fine metal particles, specifically, the shortest distance between adjoining fine metal particles means the distance between an arbitrary vertex of one fine metal particle and a vertex of another fine metal particle nearest the fine metal particle.

By arranging a plurality of fine metal particles to decrease the intervals between fine metal particles, the electric field is enhanced (surface plasmon enhancement) by dipole-dipole interaction. Further, it is possible to improve multiphoton excitation efficiency of the metal structure.

Herein, the variability in the length of the long axis and short axis of the fine metal particles, and the variability in the interval (shortest distance between vertexes) between the fine metal particles can be checked and calculated by measuring and analyzing the plasmon resonance absorption spectrum of the fabricated metal structure. In other words, incident light polarized in a predetermined direction is irradiated to the metal structure, a wavelength position of maximum absorption of the obtained plasmon resonance absorption spectrum is compared with one another, the processing resolution on the scale of nanometers is thereby achieved, and it is possible to calculate the variability in each parameter of fine metal particles. The calculation method will specifically be descried below.

(Direction of the Fine Metal Particles)

It is another feature of the fine metal particles of the present invention that the particles are arranged in a fixed direction. The "fixed direction" means that, plurality of adjoining fine metal particles are arranged along a line, wherein the diagonal vertexes of each of the particles are on the line.

In summary, the present inventors have found out that it is possible to realize high sensitivity sensing with improved wavelength selectivity for incident light and in multiphoton excitation efficiency, by using the metal structure precisely processed by controlling the material, shape, size of a plurality of fine metal particles and precisely arranging a plurality of fine metal particles in terms of interval and direction on the substrate as described above, as a sensing device. Particularly, the present inventors have found out that the wavelength selectivity of the metal structure is improved by making the shape and size of each of the fine metal particles uniform. And the present inventors have found out that the plasmon enhancing effect become remarkably high and the multi-photon excitation efficiency is dramatically enhanced by making the height of the fine metal particles and the interval between the fine metal particles fixed in predetermined ranges, respectively.

In addition, in the description, the "metal structure" means a metal assembly (fine metal particles) such as a metal nano-rod array, and is used in the meaning including a metal structure device that is a substrate on which a metal assembly (fine metal particles) is arranged. In other words, the metal structure of the present invention may include a plurality of fine metal particles, and substrates on which a plurality of fine metal particles is arranged.

Hereinafter, a manufacturing method of the metal structure (sensing device) used in the sensing apparatus of the present invention is described with reference to FIGS. 1 and 2.

FIG. 1 is a flowchart illustrating the manufacturing method of the metal structure (sensing device) according to one embodiment of the present invention. From FIG. 2A to FIG. 2E, cross sections for explaining stages in the manufacturing method of FIG. 1 are shown.

First, in step S1, solid transparent substrate 10 (for example, glass substrate) is rinsed and dried (see FIG. 2A). The rinsing and drying are adequately performed. If the surface of substrate 10 is not sufficiently rinsed, there is a risk that fine metal particle fabricated on substrate 10 may fall away from substrate 10 in subsequent steps.

Then, in step S2, a positive electronic lithography resist solution is spin-coated (rotation-coated) on the surface of substrate 10 rinsed in step S100 (process 1), and baked (heated), the resist solvent is removed, and thin resist film 20 is formed on substrate 10 (see FIG. 2B).

At this point, to implement fine patterning of fine metal particles formed in subsequent steps, the thickness of thin resist film 20 formed on substrate 10 is preferably in the order of micrometers or less. More specifically, the thickness is preferably about 200 nm or less. The present inventors have found out that, to form such a thin resist film with a thin thickness, a resist solution obtained by diluting a commercially available resist solution to two-fold with a dedicated solvent can be used in spin coating.

The reason why the thin resist film 20 is 200 nm or less to implement fine patterning of the fine metal particles is as described below. When the film thickness of the resist film is 200 nm or more, since the entire thick resist film should be exposed with the electron beam in performing drawing exposure using an electron beam, it is necessary to extremely increase the acceleration voltage of the electron beams. Generally, the spatial resolution in drawing is made finer as the acceleration voltage of the electron beam increases, but such an extremely high acceleration voltage rather reduces the spatial resolution in drawing. Therefore, to achieve the spatial resolution in precisely drawing fine metal particles of the size expected in the present invention, the acceleration voltage does not need to be extremely high. And in the acceleration voltage required in this case, the thickness of 200 nm or less is appropriate.

Then, in step S3, a predetermined pattern is drawn in thin resist film 20 formed in step S2, for example, with an electron beam exposure apparatus (not shown). Herein, the predetermined pattern is obtained by tracing the integration arrangement diagram of desired metal structure and fine metal particles.

At this point, to achieve fine patterning formation (the lengths in the long axis direction and short axis direction are both 100 nm or less) of fine metal particles in subsequent steps, it is critically important to optimize the exposure conditions of the electron beam exposure step. As a result of detailed experiments, the present inventors have found out the following optimization conditions. As the optimization conditions of exposure, it is preferable that the acceleration voltage of the electron beam is increased and that the dose rate of exposure is significantly decreased. More specifically, in the case where the acceleration voltage of the electron beam was 100 kV to 200 kV, and the dose rate of exposure was 2 $\mu C/cm^2$ or less, it was possible to form fine metal particles on the substrate. Worthy of special note is an extremely low dose rate condition. For example, as an indication, a dose rate of 1 $\mu C/cm^2$ corresponds to one-hundredth the dose rate recommended for the used resist.

The reason why the acceleration voltage of the electron beam is increased and the dose rate of exposure is significantly decreased is as described below. As described above, the processing (drawing) spatial resolution is improved as the acceleration voltage of the electron beam is increased. This is because increasing the acceleration voltage increases the speed of the electron beam and decreases the de Broglie wavelength of the electrons. Meanwhile, increasing the dose rate of exposure corresponds to increasing the exposure time. When the exposure time is longer, vibration (for example, noise of an air conditioner of the laboratory, extremely fine vibration noise of the apparatus itself and the like) of the sample itself during exposure cannot be neglected, "blurring" of ends of processing shapes occurs, and there is the fear of resulting in degradation of the processing resolution.

Further, in step S3 development of thin resist film 20 subjected to electron beam exposure drawing, rinsing and drying are performed (see FIG. 2C). In the manufacturing method, the time of development is also an important parameter, and the development time is preferably longer than the standard time in response to the low dose rate, and specifically, for example, is about thirty minutes desirably.

Then, in step S4, chromium and then a metal such as gold exhibiting plasmon resonance absorption are sequentially deposited on substrate 10 processed in step S3 by sputtering (see FIG. 2D). The chromium layer has a thickness of about 2 nm, and is capable of enhancing adhesion between the solid transparent substrate 10 and metals such as gold. The metal (gold or the like) exhibiting plasmon resonance absorption has a thickness of 10 nm to 100 nm. This thickness corresponds to the thickness (height) of the fine metal particle in completion of a metal structure. In addition, reference numeral 30 in FIG. 2D denotes the metal film (the chromium layer and metal layer of gold or the like) formed by sputtering.

Next, in step S5, excessive resist materials are removed (peeled) from substrate 10 processed in step S4, and a metal structure 100 is fabricated (see FIG. 2E). Removal of the resist in this step is called "lift off". In this lift-off, for example, substrate 10 processed in step 400 (process 4) is immersed in a chemical agent called a resist remover, and subjected to ultrasonic rinsing, and the excessive resist film is thereby removed. In this way, the metal structure 100 is completed where fine metal particles 40 are formed on substrate 10.

There is a case where the excessive resist film is not removed completely by performing ultrasonic rinsing at room temperature, and it is preferable that ultrasonic rinsing is performed while heating the resist remover to 65° C. to 70° C. so as to completely remove the excessive resist. In other words, the present inventors have found out that it is necessary to heat resist remover in addition to ultrasonic rinsing in the lift-off process. The reason why the resist film is completely removed in this process is because the resist material becomes more soluble in the solvent by performing heating in addition to ultrasonic rinsing.

Then, in step S6, evaluations are made on the fine metal particles 40 completed in step S5 by an electron microscope and optical measurement. More specifically, the fine structure of the completed fine metal particle 40 is clarified by the electron microscope, and further, a plasmon resonance absorption response of the completed metal structure 100 is evaluated by measurement of the absorption spectrum using a light microscope. Furthermore, efficiency of multiphoton absorption is also evaluated using a laser as an excitation light source.

Summarizing results of actual evaluations in step S6, first, in structure, according to the manufacturing method of a metal structure of this embodiment, it is possible to control the size (length in the long axis direction and short axis direction, and thickness) of the fabricated fine metal particles 40 on the scale of nanometers with extreme excellence. Further, it is possible to control the variability in the size (length in the long axis direction and short axis direction, and thickness) to within 5% or less. Furthermore, in the fabricated metal structure 100, it is possible to decrease the distance between adjoining fine metal particles 40 to 50 nm or less, and to control the variability in the distance to within 5% or less. Still furthermore, it is possible to align the fine metal particles 40 in their long or short axis direction. These kinds of design (size, shape, direction and interval) can be designed arbitrarily by patterning of electron beam exposure drawing.

Described herein are methods of calculating the variability of the length of the long axis and length of the short axis of the fine metal particle, and the variability in the interval between the fine metal particles. The variability in each parameter (processing resolution) of the fine metal particles is typically evaluated by directly observing the fabricated fine metal particles using an electron microscope, but is difficult to evaluate in resolution of several nanometers.

Herein, calculation of the variability in resolution of several nanometers is made by measuring and analyzing the plasmon resonance absorption spectrum of the fabricated metal structure. In other words, incident light polarized in a predetermined direction is irradiated to the metal structure, a wavelength position of maximum absorption of the obtained plasmon resonance absorption spectrum is compared with one another, the processing resolution on the scale of nanometers is thereby achieved, and it is possible to calculate the variability in each parameter of the fine metal particles. Specific descriptions are given below with reference to FIGS. 3A to 3C.

Figure 3A:
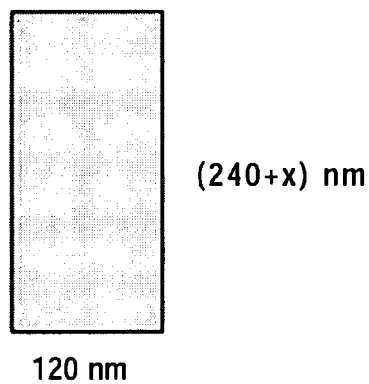
FIG. 3 contains diagrams showing an example of a calculation method using plasmon resonance absorption spectra of processing resolutions of fine metal particles.
Figure 3B:
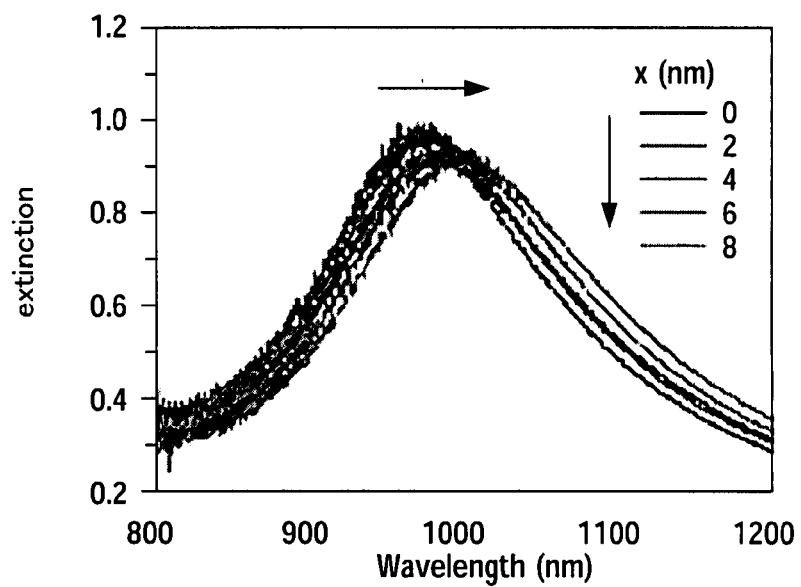
Figure 3C:
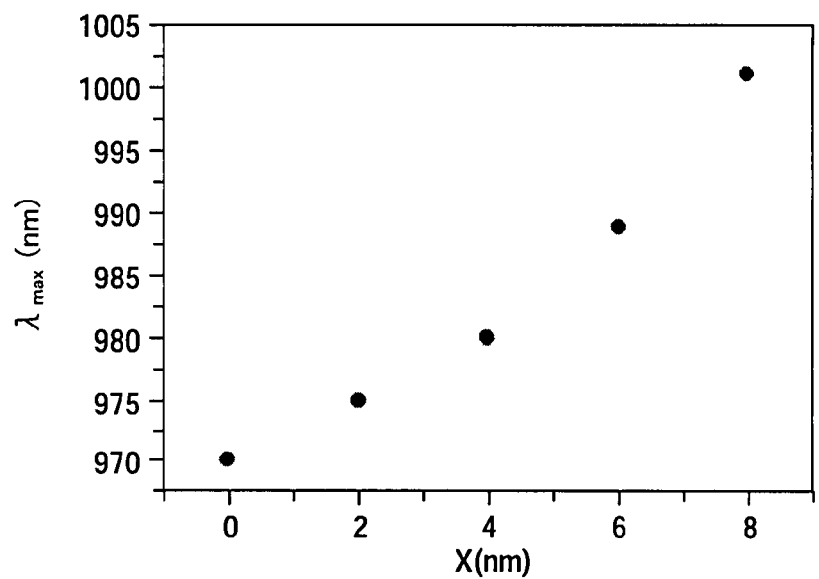

FIGS. 3A to 3C are diagrams showing an example of a calculation method of an axis length using plasmon resonance absorption spectra of processing resolutions of the fine metal particles.

FIGS. 3B and 3C show optical properties of fine metal particles in a cuboid structure designed by varying the length in the long axis direction to 240, 242, 244, 246 and 248 with the length in the short axis direction set at 120 nm as shown FIG. 3A and the height set at 120 nm and 60 nm. Herein, the length in the long axis direction of the fine metal particle is represented by 240+x(nm) and x is an integer meeting the condition of $0 \leqq 2x \leqq 8$.

FIG. 3B shows plasmon absorption spectra obtained by irradiating the incident light polarized in parallel to the long axis direction to fine metal particles with varied lengths in the long axis direction. The maximum wavelength of the plasmon absorption spectrum of the fine metal particles shifts to longer wavelengths, as the length in the long axis direction of the fine metal particles increases. The maximum wavelength of the plasmon absorption spectrum is extremely sensitive to the size (in this case, the length in the long axis direction) of the fine metal particle. Accordingly, using the maximum wavelength of the plasmon absorption spectrum, it is possible to evaluate the length in the long axis direction of the fine metal particle i.e. in this case, the processing resolution in the long axis direction.

This respect is also confirmed from FIG. 3C where the maximum wavelengths of the plasmon absorption spectra are plotted for the length of the long axis. In other words, it is possible to actually design and process the size of fine metal particle in processing resolution of 2 nm. FIGS. 3A to 3C show that the variability in each parameter of the fine metal particles can be controlled in processing resolution of at least 2 nm or less.

Evaluations of the processing resolution of the fine metal particles can be made in various variations by varying the polarization direction of the incident light irradiated to the fine metal particles. For example, it is possible to evaluate the processing resolution in the short axis direction from plasmon absorption spectra obtained by irradiating the incident light polarized parallel to the short axis direction.

Described next is a method of measuring the distance (interval) between adjoining fine metal particles that is an extremely important parameter in the metal structure of the present invention. As described above, the processing resolution for the distance (interval) between adjoining fine metal particles is typically evaluated by directly observing the fabricated fine metal particles using an electron microscope, but is difficult to evaluate in resolution of several nanometers.

Therefore, calculation of the distance between adjoining fine metal particles in resolution of several nanometers is made by measuring and analyzing the plasmon resonance absorption spectrum of the fabricated metal structure. The fine metal particles in the scale of nanometers have a property that the plasmon resonance absorption spectrum shifts by resonance plasmon interaction as the fine metal particles become closer to one another. Then, the shift amount is sensitively dependent on the distance between adjoining fine metal particles. In other words, absorption spectral measurement is made on the fabricated fine metal particles, a spot of maximum absorption of the obtained plasmon resonance absorption spectrum is compared with one another, and it is thereby possible to evaluate the distance between adjoining fine metal particles in processing resolution on the scale of nanometers. Specific descriptions are given below with reference to FIGS. 4A to 4C.

Figure 4A:
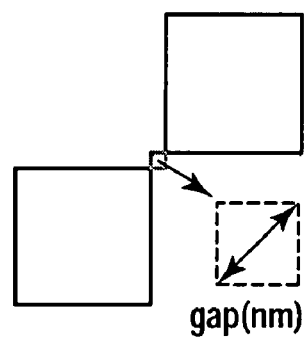
FIG. 4 contains diagrams showing an example of a calculation method of the intervals between the fine metal particles using plasmon resonance absorption spectra of processing resolutions of the fine metal particles.
Figure 4B:
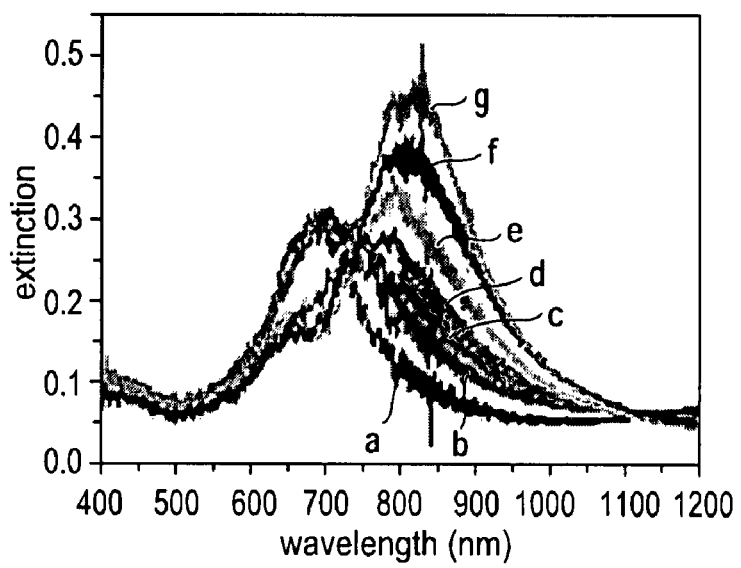
Figure 4C:
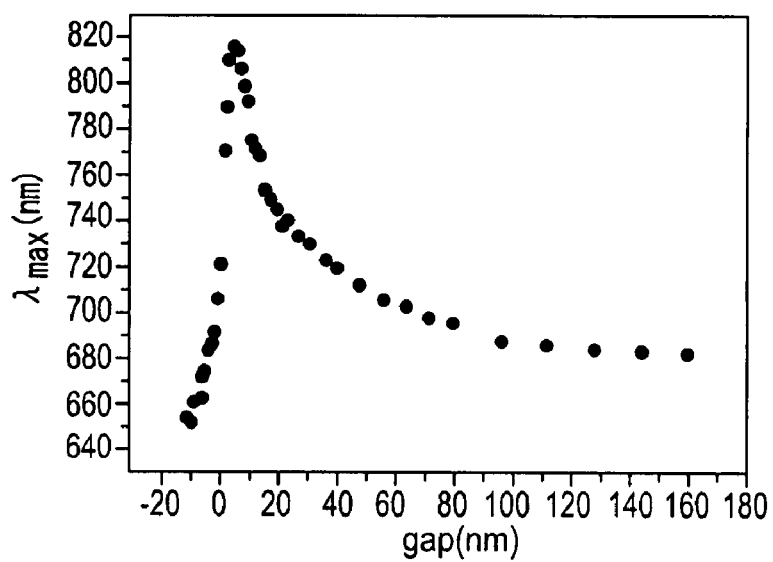

FIGS. 4A to 4C are diagrams showing an example of the calculation method for the intervals between the fine metal particles using plasmon resonance absorption spectra of processing resolutions of the fine metal particles.

As described above, the distance (interval) between adjoining fine metal particles means the shortest distance between an arbitrary vertex of a fine metal particle and the closest vertex of another fine metal particle. In FIG. 4A, this distance (interval) between fine metal particles is defined as a "gap".

FIG. 4B is a graph showing measurement results of plasmon resonance absorption spectra of the metal structure when the gap is varied to −1.8 nm, 0 nm, 0.9 nm, 1.8 nm, 2.7 nm, 3.5 nm and 5.3 nm. The spectra of FIG. 4 were measured by irradiating the incident light parallel to the two-quantity direction (the direction of the arrow) in FIG. 4A. In the spectra in FIG. 4B, "a" corresponds to −1.8 nm, "b" corresponds to 0 nm, "c" corresponds to 0.9 nm, "d" corresponds to 1.8 nm, "e" corresponds to 2.7 nm, "f" corresponds to 3.5 nm and "g" corresponds to 5.3 nm. In addition, the gap of a negative value (for example, the spectrum of a) represents that adjoining fine metal particles overlap each other.

It becomes clear from FIG. 4B that the maximum wavelength of the plasmon resonance absorption spectrum of the metal structure sensitively shifts depending on the gap. In other words, it becomes clear that the spectrum actually shifts significantly depending on changes in the distance between fine metal particles having the design size of about 0.9 nm. Further, as the gap increases, the maximum wavelength of the plasmon resonance absorption wavelengths gradually shifts to long wavelengths.

The present inventors have examined in detail the gap dependence of such a maximum wavelength of the plasmon resonance absorption spectrum over the wide gap range. FIG. 4C is a diagram illustrating the relationship between the shortest distance between fine metal particles and the maximum wavelength of the plasmon resonance absorption spectrum. FIG. 4C shows an example of examining the maximum wavelength of the plasmon resonance absorption spectrum over the gap range of −8.8 nm to 144 nm.

It becomes clear from FIG. 4C that in the gap range of −8.8 nm to 5 nm, as the gap increases, the maximum wavelength of the plasmon resonance absorption spectrum shifts to longer wavelengths, and that in the gap range of 5 nm or more, as the gap increases, the maximum wavelength of the plasmon resonance absorption spectrum shifts to shorter wavelengths. The dependence agrees with measurement results estimated by theoretical calculation.

Thus, the relationship between the shortest distance between fine metal particles and the maximum wavelength of the plasmon resonance absorption spectrum shows complicated behavior, but there are no fluctuations in measurement results, and the obtained measurement results are almost the same as theoretical values. In other words, as described in FIGS. 4A to 4C, the metal structure is fabricated that the shortest distance between fine metal particles is precisely controlled in a design size of 0.9 nm, and it shows that it is possible to control the shortest distance between fine metal particles in processing resolution of at least 0.9 nm. In addition, in the examples described later, it is explained that control of the shortest distance between fine metal particles is accurate.

Further, the metal structure fabricated according to the above-mentioned manufacturing method has the function (wavelength selectivity of optical response) exhibiting the plasmon absorption property (absorption wavelength position) significantly dependent on the size of the fine metal particle and the distance between adjoining fine metal particles. Then, the metal structure also has the efficient multiphoton absorption function with wavelength selectivity, and is capable of sensing the fluorescence from an excited absorption molecular induced by multiphoton absorption without quenching the fluorescence.

As described above with reference to FIGS. 1 to 4, it is possible to fabricate a metal structural device by preparing a large number of fine metal particles with little variability in size, making the distances between the fine metal particles uniform in the scale of nanometers, and aligning and integrating the fine metal particles on a solid transparent substrate in an arrangement where the directions of the fine metal particles are the same. It is therefore possible to realize a fine metal structure with an ideal shape and structure exhibiting the resonance plasmon optical response property having excellent wavelength selectivity and high multiphoton excitation efficiency.

The sensing device of the present invention is capable of being used for any sensing applications, and preferably applied to a sensing method as described below or used as a member of a sensing apparatus.

2. The Sensing Method of the Present Invention

It is a feature of the sensing method of the present invention to sense a sensing-target substance using an optical response of the sensing-target substance enhanced by the sensing device. More specifically, for example, the method includes 1) a step of providing the above-mentioned sensing device with a sensing-target substance adsorbed thereto, 2) a step of irradiating excitation light to the prepared sensing device, and 3) a step of measuring an optical response from the sensing-target substance, so as to sense (quantitatively and qualitatively) the sensing-target substance.

The optical response used as a response signal in the sensing method of the present invention is selected as appropriate corresponding to the kind of the sensing-target substance, and for example, may be fluorescence, optical scattering (including Raman scattering), resonance absorption, high-frequency emission, sum frequency, difference frequency and the like. When the sensing-target substance is a fluorescent molecule or a molecule labeled with a fluorescent substance, the response signal can be fluorescence. When the sensing-target substance is a biomolecule such as DNA, enzyme and the like, the response signal can be Raman scattering. In the sensing method of the present invention, it is possible to use fluorescence by multiphoton absorption as a response signal.

Sensing-target substance adsorbed to the sensing device is not limited particularly, and for example, can be fluorescent molecule or molecule labeled with fluorescent substance when the response signal is fluorescence, and can be biomolecule, when the response signal is Raman scattering. Means for making the sensing-target substance adsorbed to the sensing device is not limited particularly, and for example, a solution including the sensing-target substance may be dropped onto the device.

The light irradiated to the sensing device is preferably irradiated in the direction perpendicular to the sensor device substrate. Further, irrespective of the polarization direction and type of the incident light such as unpolarized light, circularly polarized light, elliptically polarized light, and linearly polarized light, the sensing device exhibits adequate functions.

Preferably, the light irradiated to the sensing device is able to excite the sensing-target substance. Examples of excitation include fluorescence excitation causing fluorescence, elementary excitation causing Raman scattering and the like. Examples of fluorescent excitation include one-photon excitation and multi-photon excitation (including two-photon excitation).

The light irradiated to the sensing device is selected as appropriate corresponding to the type of the sensing-target substance, and the constitution of the metal structure included in the sensing device. The irradiated light (excitation light) will be described below in the case of using fluorescence as a response signal.

Described first is the case where the optical response is fluorescence based on one-photon absorption.

In this case, the wavelength of excitation light is preferably set according to a plasmon resonance absorption wavelength range of the metal structure that is the sensing device. Particularly, when the absorption spectrum of the sensing-target substance at least partially overlaps the plasmon resonance absorption spectrum of the metal structure, the excitation wavelength of the excitation light is preferably set at a value in accordance with the overlapping wavelength range. By this means, it is possible to measure the extremely enhanced fluorescence from the sensing-target substance adsorbed to the metal structure that is the sensing device, and to sense the sensing-target substance.

Further, in the case where the optical response is fluorescence based on one-photon absorption, when maximum absorption of the plasmon resonance absorption spectrum of the metal structure that is the sensing device differs largely (for example, 200 nm or more) from maximum absorption of the absorption spectrum of the sensing-target substance, the wavelength of the excitation light is preferably set at a value in accordance with the absorption wavelength range of the sensing-target substance. Since the wavelength range of the plasmon resonance absorption spectrum of the metal structure is extremely wide, even when the wavelength of the excitation light differs largely from maximum absorption of the plasmon resonance absorption spectrum of the metal structure, it is possible to resonance-excite the plasmon of the metal structure to some extent. In this case, excitation efficiency decreases as compared with the case that the absorption spectrum of the sensing-target substance overlaps the plasmon resonance absorption spectrum of the metal structure, but it is possible to measure the fluorescence enhanced by plasmon resonance absorption in sufficient intensity, and to adequately sense the sensing-target substance.

Described next is the case where the optical response is fluorescence based on multiphoton absorption.

In this case, the wavelength of excitation light is preferably set at a value in accordance with a resonance absorption wavelength range of the plasmon resonance absorption spectrum of the metal structure that is the sensing device. Further, in fluorescent sensing based on multiphoton absorption, even when maximum absorption of the plasmon resonance absorption spectrum of the metal structure differs largely from maximum absorption of the absorption spectrum of the sensing-target substance, a picosecond or femtosecond pulse laser is used for excitation light, efficient multi-photon absorption is thereby induced via surface plasmon, and it is possible to measure remarkably enhanced fluorescence from the sensing-target substance and adequately sense the sensing-target substance.

Thus, in the sensing method of the present invention, since the above-mentioned sensing device is used, irrespective of the absorption spectrum of the sensing-target substance, it is possible to perform high sensitivity sensing. In other words, the sensing method of the present invention provides an advantage of enabling sensing-target substances to be sensed with efficiency even when the sensing-target substances have absorption in any wavelength ranges (in other words, in any correlation in wavelength between the absorption spectrum of the sensing-target substance and the plasmon resonance absorption spectrum of the metal structure that is the sensing device.)

According to the sensing method of the present invention, it is possible to perform quantification or qualification of the sensing-target substance. For example, it is possible to perform quantification by measuring the intensity of the optical response, and to perform qualification by measuring the spectrum of the optical response. In the case of quantification of the sensing-target substance, a calibration curve may be used that indicates the relationship between the intensity of the optical response and the quantity of the sensing-target substance. Further, since the spectrum of optical response is specific to the substance, in the case of performing qualification of the sensing-target substance, the measured spectrum can be compared with the previously confirmed spectrum of the optical response of the sensing-target substance.

3. The Sensing Apparatus of the Present Invention

Described next is the sensing apparatus using the above-mentioned metal structure as a sensing device. The sensing apparatus using fluorescence as a response signal will be described below as an example, but, naturally, the response signal is not limited to fluorescence. For example, the sensing apparatus of the present invention is capable of being apparatus for measuring optical scattering (Raman scattering), long-wavelength emission, sum frequency, difference frequency and the like to sense a sensing-target substance.

Figure 5:
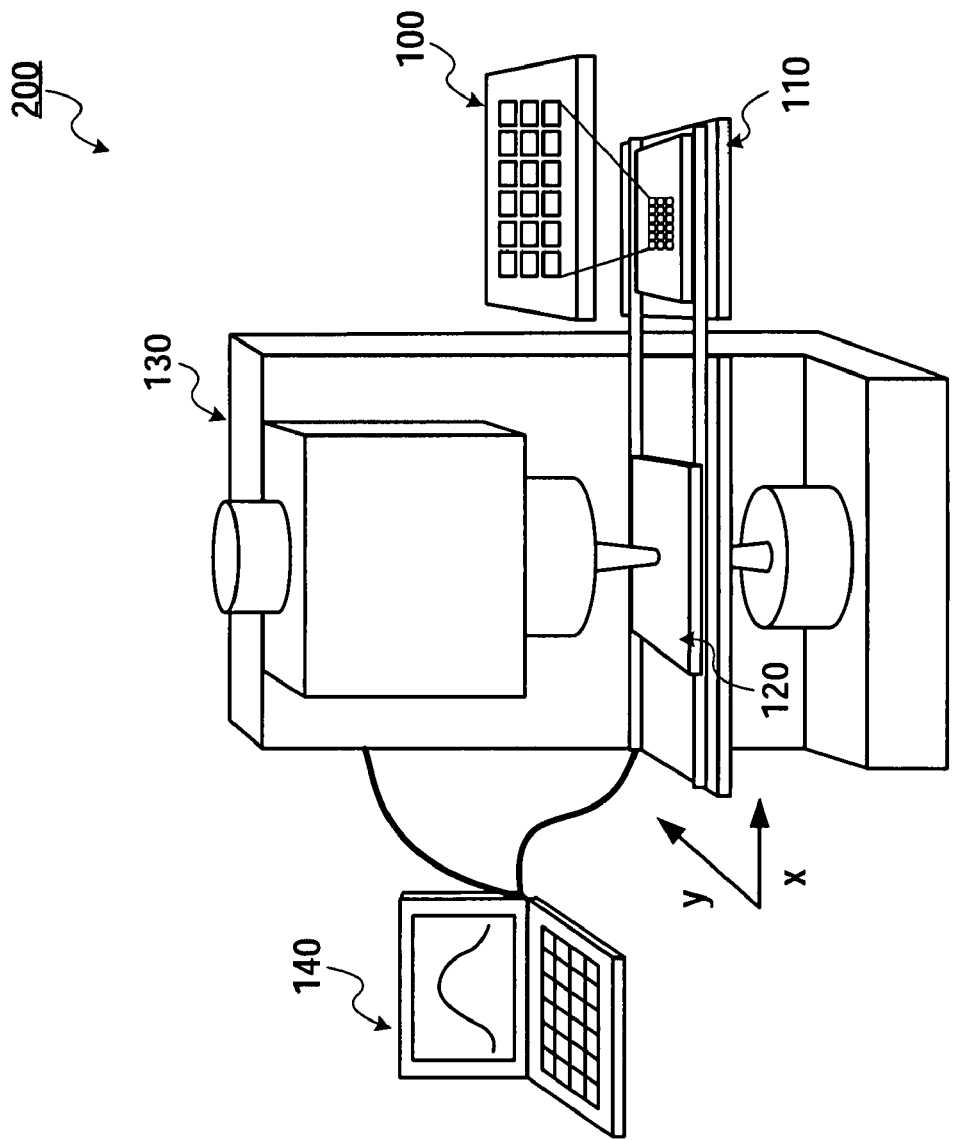
FIG. 5 is a diagram showing an example of an entire configuration of a sensing apparatus according to one embodiment of the present invention.

FIG. 5 is a diagram showing an example of an entire configuration of a sensing apparatus according to one embodiment of the present invention. In the example of FIG. 5, described is the sensing apparatus for irradiating excitation light to a sample labeled with a fluorescent molecule on the surface of metal structure 100, and measuring an amount of excited fluorescence to perform sensing.

In FIG. 5, sensing apparatus 200 has metal structure 100, substrate transfer section 110, stage 120, fluorescence intensity measuring section 130 and computer 140.

As described above, metal structure 100 has a configuration where fine metal particles are precisely arranged in terms of interval between adjoining fine metal particles and the direction of them on the substrate, wherein the fine metal particles are appropriately controlled in material, shape, size, and functions as a sensing device of sensing apparatus 200. A sample including the sensing-target substance labeled with a fluorescent molecule is adsorbed to the surface of metal structure 100, and installed in substrate transfer section 110. Herein, the fluorescent molecule labels selectively the sensing-target substance among the sample adsorbed to the surface of metal structure 100.

Substrate transfer section 110 transfers installed metal structure 100 onto stage 120. Further, substrate transfer section 110 is capable of simultaneously transferring a plurality of metal structures 100 onto stage 120 so as to sense a plurality of sensing-target substances at the same time.

Metal structure 100 transferred from substrate transfer section 110 is mounted on stage 120, and stage 120 travels in parallel on the XY plane, to vary the irradiating position of the excitation light irradiated to metal structure 100 inside the fluorescence intensity measuring section 130. Stage 120 is controlled by computer 140, and is capable of traveling on the XY plane with high driving resolution.

Fluorescence intensity measuring section 130 irradiates the excitation light to metal structure 100 mounted on stage 120, and measures the intensity of the excited fluorescence. Further, fluorescence intensity measuring section 130 is capable of sensing quantitatively the sensing-target substance adsorbed to metal structure 100 by measuring the intensity of the excited fluorescence.

Figure 6:
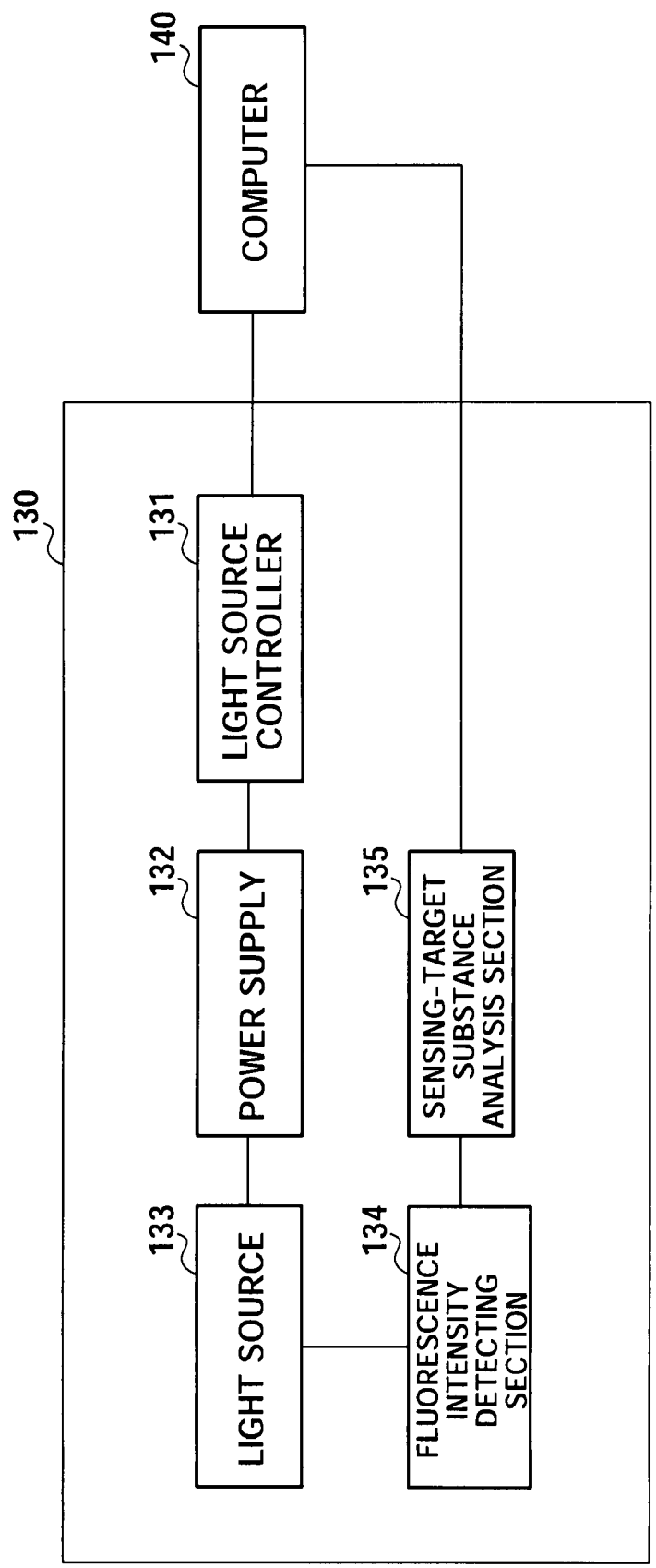
FIG. 6 is a functional block diagram showing functions of a fluorescence intensity measuring section.

Herein, fluorescence intensity measuring section 130 is specifically described with reference to FIG. 6. FIG. 6 is a functional block diagram showing functions of fluorescence intensity measuring section 130.

In FIG. 6, fluorescence intensity measuring section 130 has light source controller 131, power supply 132, light source 133, fluorescence intensity detecting section 134 and sensing-target substance analysis section 135.

Light source controller 131 is controlled by computer 140, and adjusts the output voltage of power supply 132. The excitation wavelength of the excitation light irradiated from light source 133 is thereby controlled.

Power supply 132 supplies voltage to light source 133.

Light source 133 irradiates the excitation light to metal structure 100 mounted on stage 120. The wavelength of the excitation light is controlled to a suitable wavelength to be absorbed by the sensing-target substrate adsorbed to metal structure 100. Further, control of the excitation wavelength of the excitation light can be different between the case of performing fluorescent sensing based on one-photon absorption and the case of performing fluorescent sensing based on multiphoton absorption. As described previously, the excitation wavelength of the excitation light irradiated from light source 133 is controlled as appropriate corresponding to the absorption spectrum of the sensing-target substance and the plasmon resonance absorption spectrum of metal structure 100.

Florescence intensity detecting section 134 detects the intensity of the fluorescence emitted by the sensing-target substance after absorbing the excitation light from light source 133.

Sensing-target substance analysis section 135 analyzes the intensity of the fluorescence detected in fluorescence intensity detecting section 134, and quantitatively calculates the sensing-target substance adsorbed to metal structure 100. For example, quantitative calculation of the sensing-target substance by sensing-target substance analysis section 135 is performed using a calibration curve that indicates the relationship between the intensity of the fluorescence and the quantity of the sensing-target substance. The calibration curve may be stored in storage means (not shown) that fluorescence intensity measuring section 130 holds for each sensing-target substance. Further, sensing-target substance analysis section 135 outputs a calculation result of the sensing-target substance to computer 140.

Computer 140 performs various kinds of control for stage 120, and fluorescence intensity measuring section 130. More specifically, computer 140 controls light source controller 131 to adjust the excitation wavelength of the excitation light irradiated from light source 133. Further, computer 140 displays the calculation result of the sensing-target substance calculated in sensing-target substance analysis section 135. In addition, an input of an operation signal to computer 140 is made by a user via an interface (not shown).

The operation of sensing apparatus 200 configured as described above will specifically be described below with reference to FIG. 7.

Figure 7:
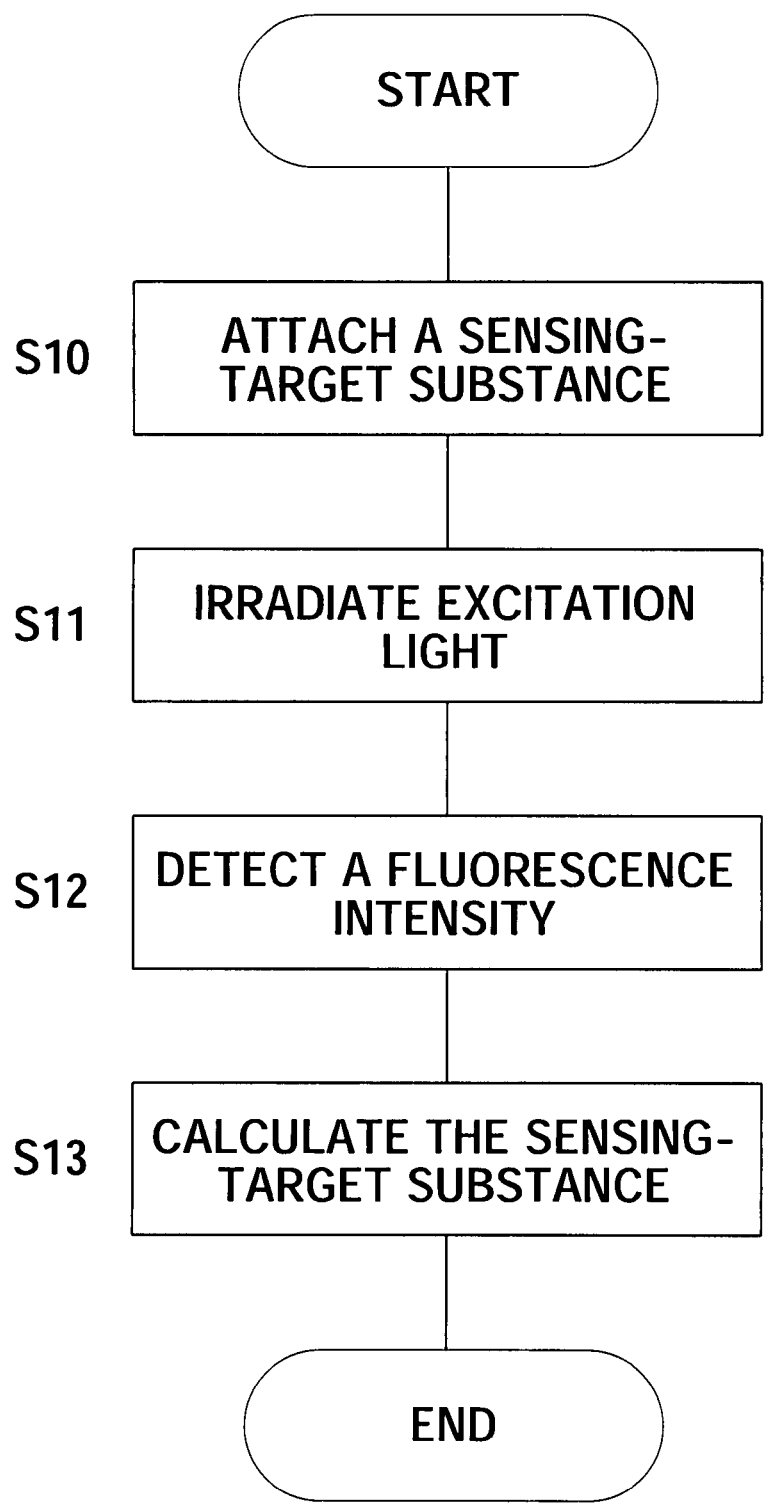
FIG. 7 is a flowchart showing an example of the operation of the sensing apparatus of FIG. 5.

FIG. 7 is a flowchart illustrating an example of the operation of sensing apparatus 200 of FIG. 5.

First, a sample containing a sensing-target substance labeled with a fluorescent molecule is adsorbed to the surface of metal structure 100, and this metal structure 100 is mounted on stage 120 via substrate transfer section 110 (S10).

When metal structure 100 is mounted on stage 120, light source 133 of fluorescence intensity measuring section 130 irradiates excitation light to metal structure 100 (S11) so as to excite the sensing-target substance. At this point, stage 120 travels in parallel on the XY plane while being controlled by computer 140, and thereby the irradiating position of the excitation light to metal structure 100 varies. The excitation light irradiated from light source 133 is controlled to have a suitable excitation wavelength such that the sensing-target substance emits the fluorescence by absorbing the light.

Next, fluorescence intensity detecting section 134 detects the intensity of the fluorescence that the sensing-target substance emits by absorbing the excitation light from light source 133 (S12), and sensing-target substance analysis section 135 analyzes the intensity of the fluorescence detected in fluorescence intensity detecting section 134, and calculates quantitatively the sensing-target substance adsorbed to metal structure 100 (S13). The calculated amount of the sensing-target substance adsorbed to metal structure is displayed by computer 140.

As described previously, the excitation wavelength of the excitation light irradiated from light source 133 can be different between the case of performing fluorescent sensing based on one-photon absorption and the case of performing fluorescent sensing based on multi-photon absorption.

In addition, this embodiment describes metal structure 100 as a sensing device used in fluorescent sensing, but applications of metal structure 100 are not limited to this case. For example, metal structure 100 is applicable to sensing devices of sensing apparatuses for detecting optical scattering (Raman scattering), long-wavelength emission, sum frequency, difference frequency and the like to perform sensing.

Thus, according to this embodiment, a metal structural device is fabricated by preparing a large number of fine metal particles with little variability in the size, making distances between the fine metal particles uniform in the scale of nanometers, and aligning and integrating the fine metal particles on a solid transparent substrate in an arrangement where the directions of the fine metal particles are the same, and it is thereby possible to realize the fine metals structure with the ideal shape and structure exhibiting the resonance plasmon optical response property having excellent wavelength selectivity and high multiphoton excitation efficiency.

Further, according to this embodiment, such a metal structure is applied to a sensing apparatus as a sensing device, and it is thereby possible to realize the sensing apparatus for fluorescent sensing and the like with high sensitivity.

EXAMPLES

More specific embodiments (examples) of the present invention will be described below. However, the present invention is not understood by being limited to the Examples as described below.

Example 1

In this example, fine metal particles were fabricated on a glass substrate (Matsunami Glass: 24 mm×24 mm) by electron-beam lithography/lift-off. More specifically, the glass substrate was subjected to ultrasonic rinsing with acetone, methanol, and pure water in this order, and a positive electron-beam lithography resist (ZEP-520A, Zeon corporation, diluted to two parts of a dedicated thinner) was spin-coated (initial: 1000 rpm for 10 sec. main: 4000 rpm for 90 sec.) on the glass substrate, and was pre-baked at 180° C. for 3 minutes on a hot plate. Next, a predetermined pattern was drawn at a dose rate of 1.2 $\mu C/cm^2$ using an electron beam exposure apparatus with the acceleration voltage of 100 kV, and developed for 30 minutes. Next, 2 nm of chromium and 10 nm to 100 nm of gold were deposited on the developed and rinsed substrate by sputtering, and lift-off was performed in a resist remover solution (dimethylformamide). At this point, by applying ultrasonic waves for 5 minutes while heating the resist remover to high temperatures of 65° C. to 75° C., fabricating a fine metals structure (sensing device) succeeded with no resist left.

The size of the fabricated fine metal particle was several tens to several hundreds of nanometers, wherein the size means the length in the long axis direction, the length in the short axis direction and the thickness (height from the surface of the substrate) And design of distances between fine metal particles was made on the scale of the order of nanometers. In this way, metal structures having various kinds of fine metal particles were fabricated with different lengths in the long axis/short axis directions, thicknesses of fine metal particle, and interval (distance) between adjoining fine metal particles.

Figure 8B:
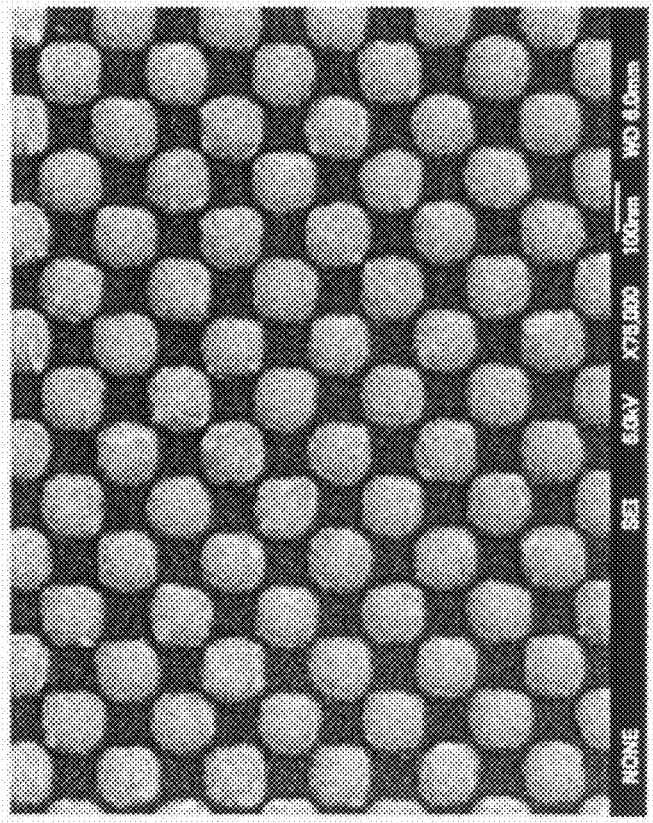
FIG. 8 shows electron microscope photographs of typical metal structures (sensing devices) actually fabricated.
Figure 8A:
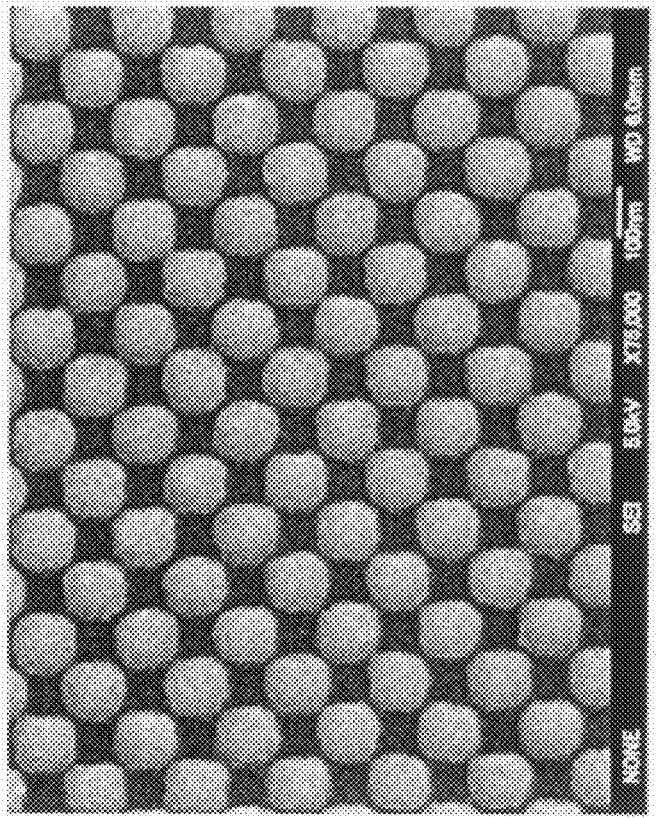

FIGS. 8A and 8B are electron microscope photographs of typical metal structures (sensing devices) actually fabricated. Particularly, FIG. 8A shows the case where the thickness of the fine metal particle was 40 nm, the long axis and short axis of the fine metal particle were both 100 nm, and the distance (interval) between adjoining fine metal particles was 4 nm, and FIG. 8B shows the case where the thickness of the fine metal particle was 40 nm, the long axis and short axis of the fine metal particle were both 100 nm, and the distance (interval) between adjoining fine metal particles was 10 nm.

From FIGS. 8A and 8B, it has been demonstrated that the fine metal particles precisely controlled in size and shape are integrated on the substrate at regular intervals in the certain direction orderly, and that it is possible to fabricate the excellent metal structure (sensing device) by the present invention.

Herein, according to the theory of the present invention as described above, by making the distance (interval) between fine metal particles small, the electric field is enhanced (surface plasmon enhancement) by dipole-dipole interaction. The distances between adjoining fine metal particles of FIGS. 8A and 8B are 4 nm and 10 nm respectively. Therefore the metal structure of FIG. 8A is considered functioning as a sensing device with higher sensitivity than the metal structure of FIG. 8B.

Therefore, the present inventors made in detail optical response evaluations of the metal structure (sensing device) fabricated in the above-mentioned steps. Particularly, with attention directed toward a correlation between the plasmon resonance absorption property on the distance (interval) between adjoining fine metal particles, experiments were performed. Further, evaluations were made on multiphoton absorption and fluorescence efficiency.

Figure 9A:
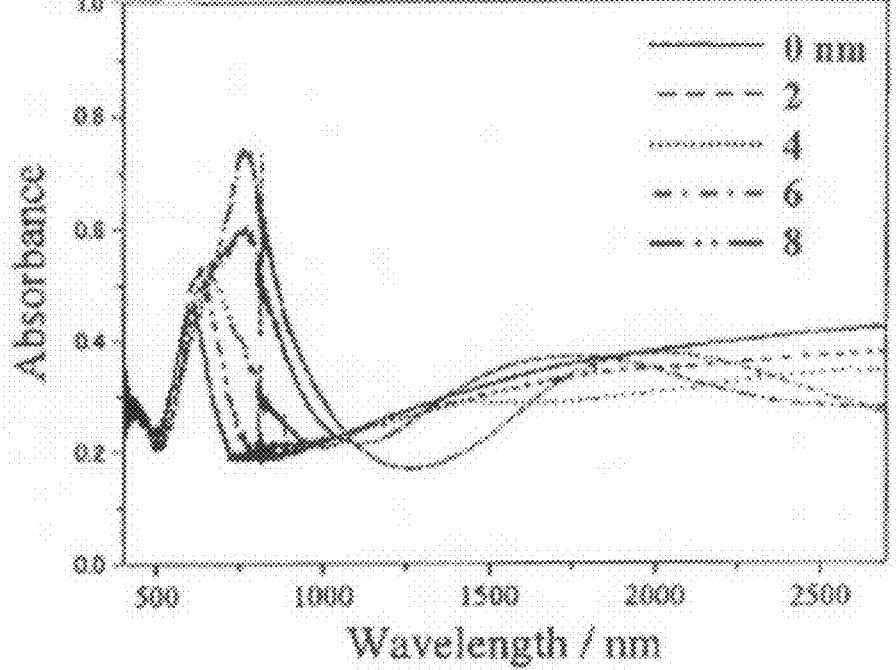
FIG. 9 shows graphs illustrating the relationship between the resonance plasmon absorption spectrum of the metal structure and the gap distance of adjoining fine metal particles contained in the metal structure.
Figure 9B:
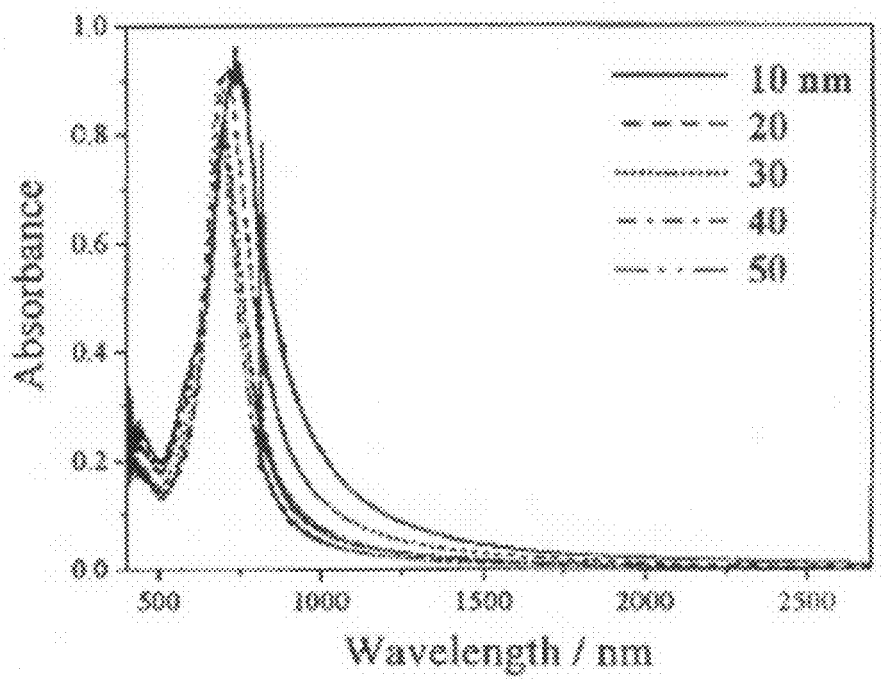

FIGS. 9A and 9B are graphs illustrating the relationship between the resonance plasmon absorption spectrum of the metal structure and the gap of fine metal particles contained in the metal structure. FIG. 9A shows plasmon resonance absorption spectra when the interval between fine metal particles with a thickness of 40 nm and the long axis and short axis of both 100 nm were changed to 0 nm, 2 nm, 4 nm, 6 nm and 8 nm. Further, FIG. 9B shows plasmon resonance absorption spectra when intervals of fine metal particles with a thickness of 40 nm and the long axis and short axis of both 100 nm were changed to 10 nm, 20 nm, 30 nm, 40 nm and 50 nm.

Figure 10:
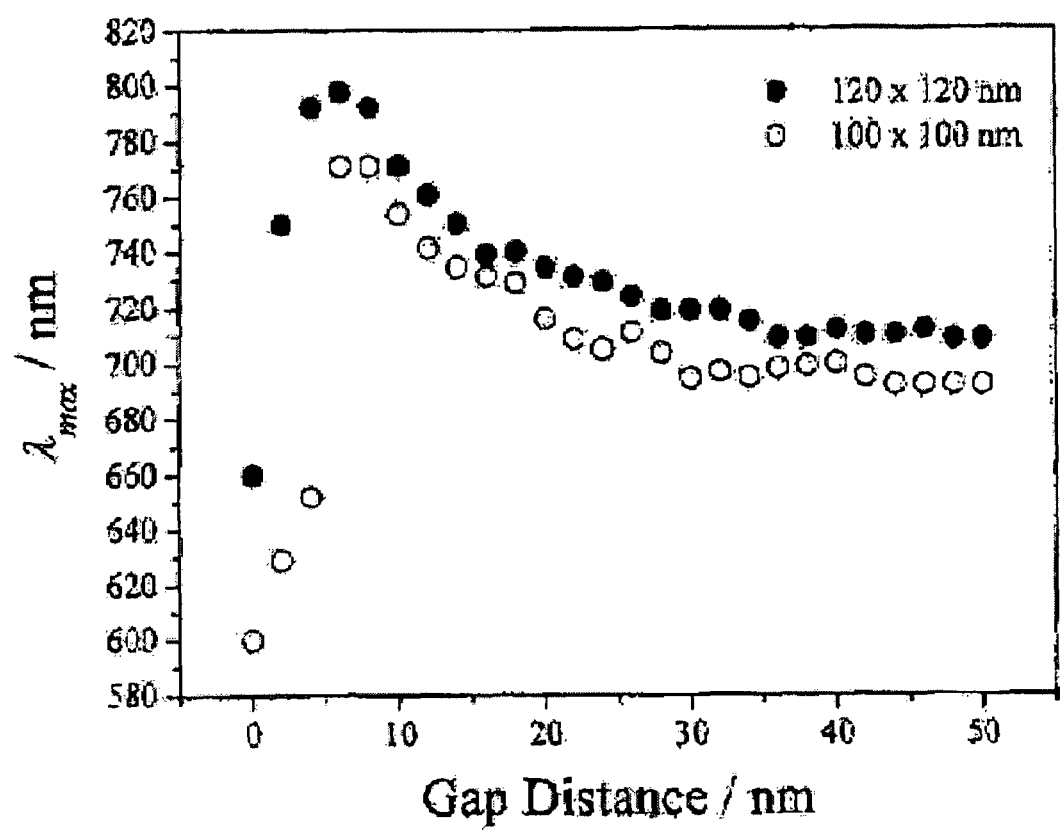
FIG. 10 shows a graph illustrating the relationship between the gap between adjoining fine metal particles and the maximum wavelength of the resonance plasmon absorption spectrum of the metal structure.

FIG. 10 shows a graph illustrating the relationship between the interval between adjoining fine metal particles and the maximum wavelength of the resonance plasmon absorption spectrum of the metal structure. In other words, in FIG. 10, the dependence of the maximum wavelength on the distance between adjoining fine metal particles was studied.

From FIGS. 9A, 9B and 10, it has been shown that when the distance between fine metal particles is less than 10 nm, the electric field is extremely enhanced in a wide wavelength range. Further, in this region, as the distance between fine metal particles increases, the absorption maximum wavelength shifts to longer wavelengths. Further, it became clear that in the case where the distance between fine metal particles is 10 nm or more, as the distance between fine metal particles increases, the absorption maximum wavelength shifts to shorter wavelengths; and that when the distance between fine metal particles exceeds about 30 nm, the absorption maximum wavelength converges to an almost constant value (700 nm). Thus, the present inventors succeeded in controlling the resonance plasmon absorption wavelength by regulating the distance (interval) between adjoining fine metal particles.

Example 2

The present inventors further performed experiments on multiphoton excitation efficiency and fluorescence enhancement of the metal structures (sensing devices) fabricated by the method.

The present inventors have fabricated a metal structure such that the thickness, the length of the long axis and the length of the short axis of each fine metal particle was constant and that the distance between adjoining fine metal particles was only varied, and examined multiphoton excitation efficiency and fluorescence enhancement of these metal structures.

Figure 11:
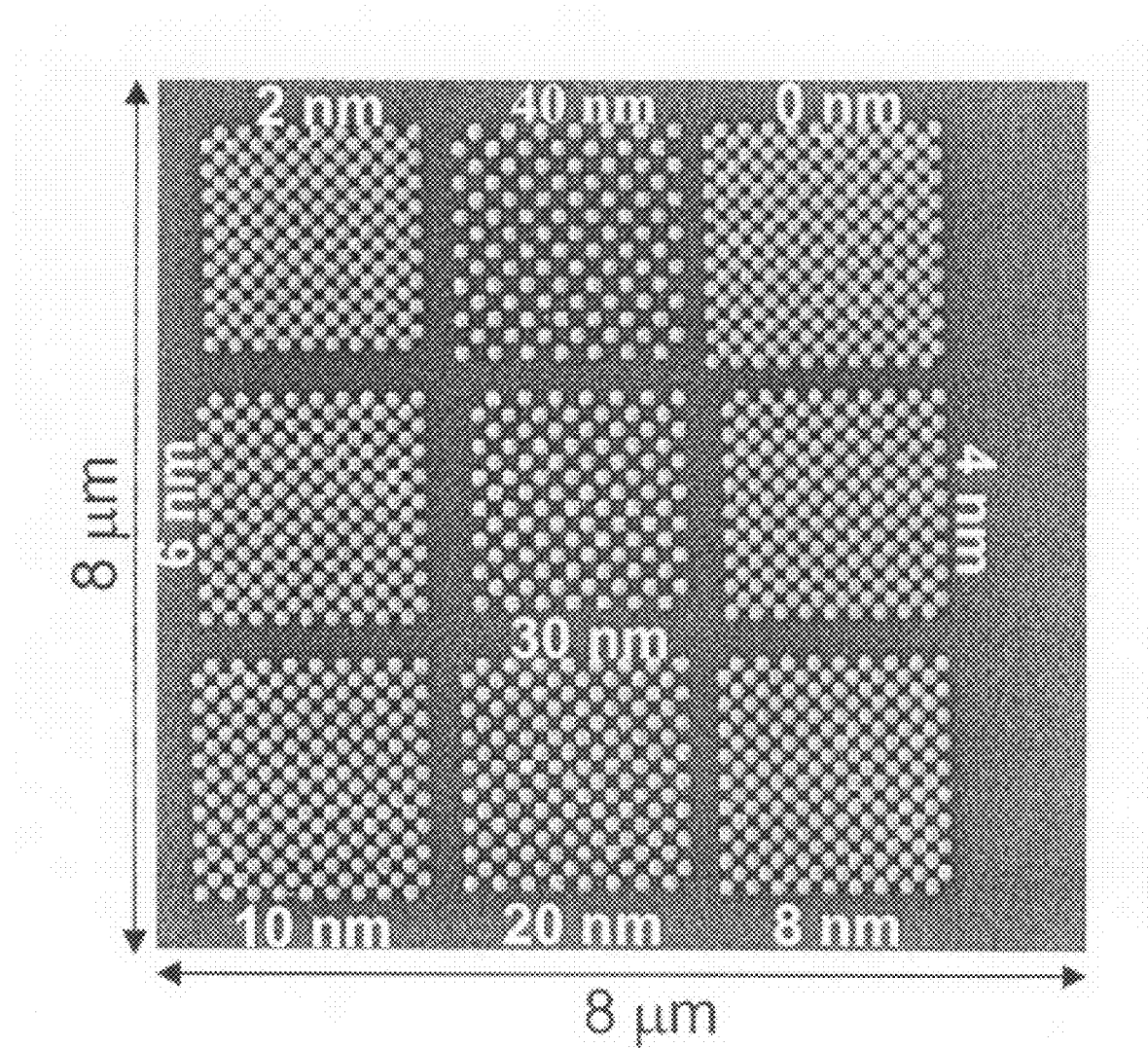
FIG. 11 is an electron microscope photograph of a metal structure where fine metal particles with various gap distances are formed integrally.

FIG. 11 is an electron microscope photograph of a metal structure where fine metal particles with various gaps are formed integrally. Figures (0 nm, 2 nm, 4 nm, 6 nm, 8 nm, 10 nm, 20 nm, 30 nm and 40 nm) shown in FIG. 11 are distances between respective adjoining fine metal particles. The long axis and short axis of each of the fine metal particles were 100 nm, and the thickness thereof was 40 nm.

After making dye (1,4-Bis(bis(dibutylamino)styryl)-2,5-dimethoxybenzene) adsorbed to the metal structure as shown in FIG. 11, a femtosecond pulse laser with a wavelength of 800 nm and a pulse width of 100 femtoseconds was irradiated under the microscope. This dye does not have one-photon absorption in the above-mentioned laser wavelength, and when excited, its excitation is all by multiphoton excitation. As a result of the experiments, the fluorescence was observed actually from the dye, and it has been shown that multiphoton excitation by resonance plasmon enhancement is induced. In addition, the spectrum of the observed fluorescence agrees with the spectrum in one-photon excitation.

Figure 12:
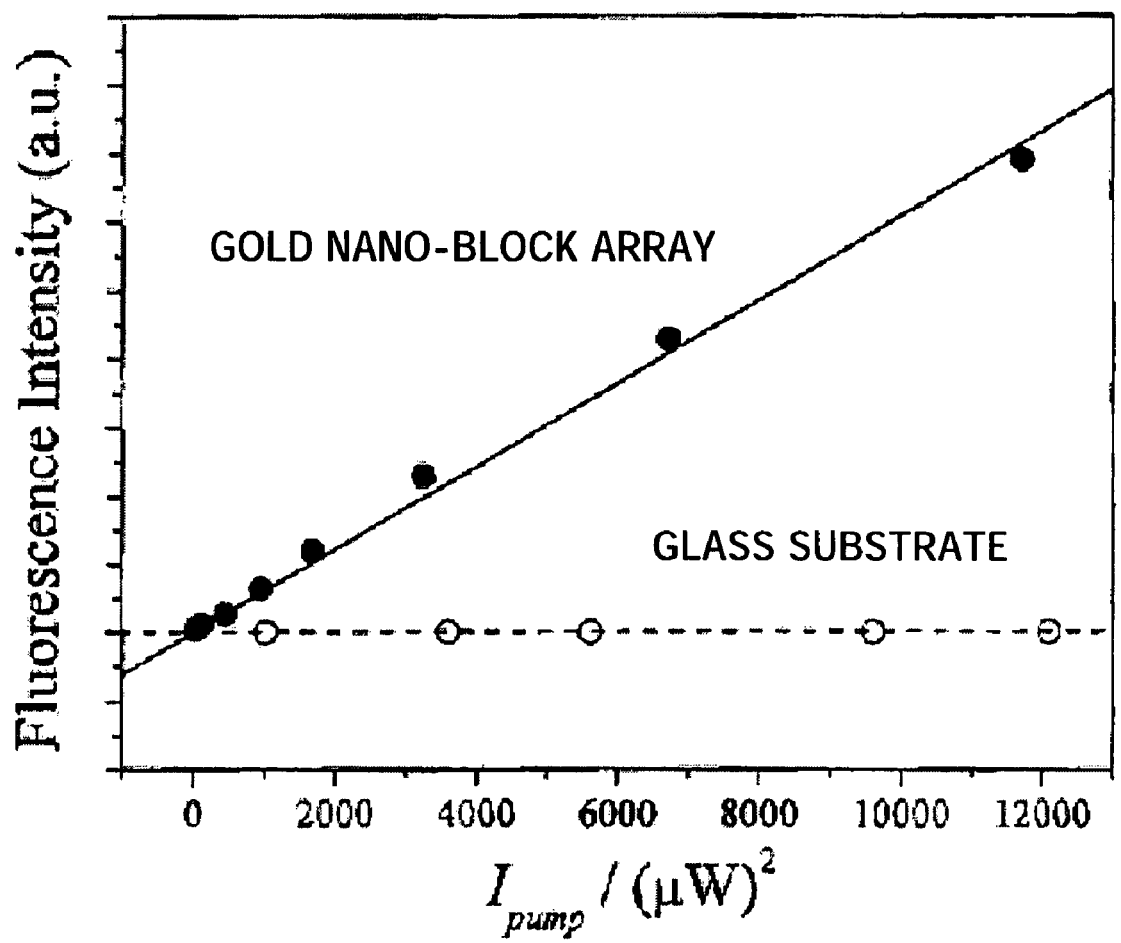
FIG. 12 is a graph illustrating the relationship between the intensity of an excitation laser beam irradiated to the metal structure and the intensity of multiphoton excitation fluorescence of dye on the metal structure.

The dependence of obtained fluorescence intensity through multiphoton excitation on excitation laser light intensity was investigated and a result of the investigation is shown in FIG. 12.

FIG. 12 is a graph illustrating the relationship between the intensity of the excitation laser light irradiated to the metal structure and the intensity of the multiphoton excitation fluorescence of the dye on the metal structure. In FIG. 12, the horizontal axis represents the square of the intensity of the excitation laser light, and the vertical axis represents the fluorescence intensity of the dye from the metal structure. In addition, in FIG. 12, results are also plotted in similar experiments of the dye on a glass substrate for comparison.

As shown in FIG. 12, the multiphoton excitation fluorescence intensity from the metal structure shows a clear linear relationship with respect to the square of the excitation laser light intensity, and it has been clarified that the fluorescence from the metal structure is based on two-photon excitation. The efficiency of enhancement exceeds four hundreds times at the maximum. Further, in such a metal structure, the present inventors have found out that emission in the visible range of the fine metal particles is also extremely intensified.

Further, the present inventors studied in detail the dependence of fluorescence enhancement efficiency of two-photon excitation on the height of the fine metal particle (thickness of the fine metal particle) in the metal structure as shown in FIG. 11.

Figure 13:
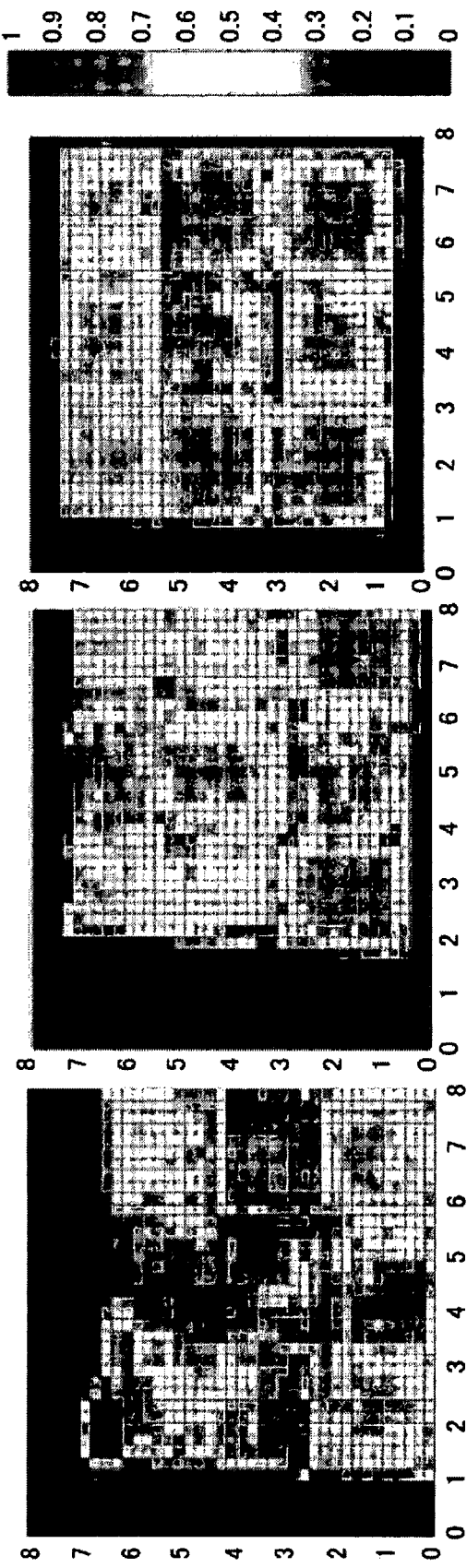
FIG. 13 contains views showing two-photon fluorescence mapping images of the metal structure with dye adsorbed thereto.

FIGS. 13A to 13B are views showing two-photon fluorescence mapping images of the metal structure with dye adsorbed thereto. FIG. 13A shows the case where the thickness of the fine metal particle is 40 nm, FIG. 13B shows the case where the thickness of the fine metal particle is 60 nm, and FIG. 13C shows the case where the thickness of the fine metal particle is 100 nm.

From FIGS. 13A to 13C, obvious fluorescence enhancement is observed in the fine metal particles with the thickness of 40 nm; meanwhile, as the thickness of the fine metal particle increases to 60 nm and 80 nm, the fluorescence enhancing effect is harder to observe. Further, in the case of FIG. 13A with the most remarkable enhancing effect (the thickness of the fine metal particle=40 nm), even when the distances between adjoining fine metal particles are 2 nm, 4 nm and 6 nm, and thus extremely small, the remarkable enhancing effect is clearly shown.

Thus, the present inventors have found out the size and shape of fine metal particle and gap of the fine metal particles to maximize the effect in two-photon excitation fluorescence detection by surface enhancement plasmon.

It was thus made clear that the thickness of the fine metal particle is an important factor in implementing the sensing device for performing high sensitivity sensing. Therefore, dependence of the resonance plasmon absorption spectrum on the thickness of fine metal particle was examined while defining the long axis and short axis of fine metal particle to 120 nm and the gap of fine metal particles to 200 nm.

Figure 14:
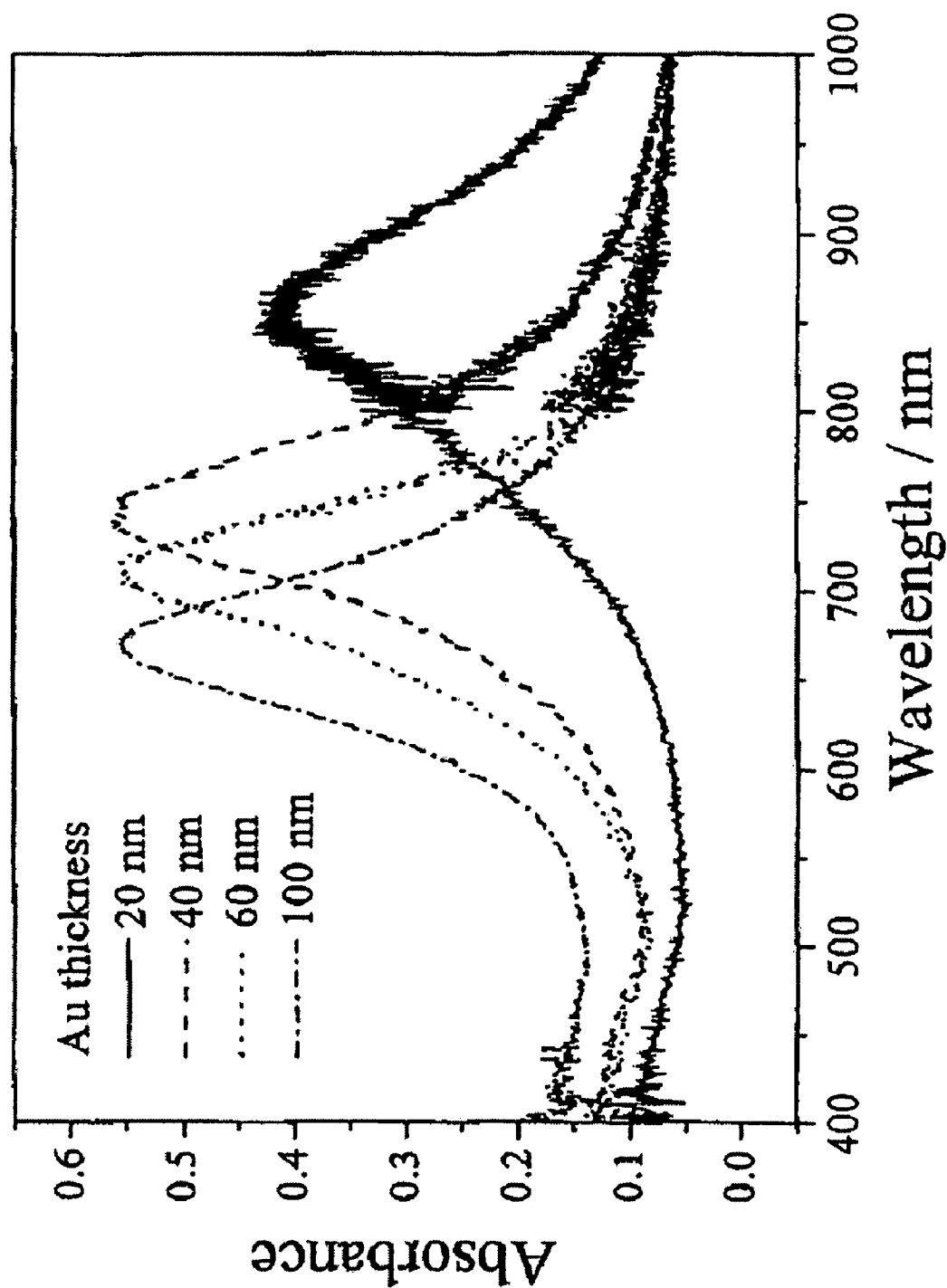
FIG. 14 is a graph illustrating the relationship between the resonance plasmon absorption spectrum of the metal structure and the thickness of the fine metal particle.

FIG. 14 is a graph illustrating the relationship between the resonance plasmon absorption spectrum of the metal structure and the thickness of the fine metal particle. In FIG. 14, the plasmon resonance absorption spectra were observed with the thickness of the fine metal particle changed to 20 nm, 40 nm, 60 nm, and 100 nm.

From FIG. 14, it was made clear that the resonance plasmon absorption wavelength is capable of being controlled by changing the thickness of the fine metal particle. Further, as the resonance plasmon absorption wavelength approaches the excitation laser wavelength (800 nm), the fluorescence enhancing effect is more remarkable. Actually, in the metal structure (the thickness of the fine metal particle was 40 nm) where the resonance plasmon absorption wavelength is nearest the excitation laser light, it was possible to obtain the enhancing effect of eight hundreds times.

Example 3

In this Example, fine metal particles were fabricated on a glass substrate with the design of the long axis and short axis of both 80 nm and the distance between fine metal particles of 4 nm. First, DNA (1 mmol/l) with thiol modified at 3' end of 40 base pairs was dropped onto the glass substrate, and the glass substrate was allowed to stand in an incubator of 37° C. for 12 hours to induce coupling to gold. Next, complementary DNA was allowed to stand in a buffer of pH7.4 at 37° C. to induce hybridization. Then, the metal structure was slowly stirred three times each for 5 minutes in a surfactant solution (sodium dodecyl sulphate, SDS solution) and rinsed, SYBR Green (Molecular Probes, Inc.) was diluted to 1000 parts of dimethyl sulfoxide (DMSO) and dropped onto the metal structure, and the metal structure was rinsed by the surfactant solution in the same way as described above ten minutes later. The measurement system was the same as described above.

Then, the fabricated sample was subjected to fluorescence intensity mapping of single strand DNA (ssDNA) and double strand DNA (dsDNA). The SYBR Green I dye intercalated in DNA emits strong florescence, and the SYBR Green I dye absorbed by dsDNA shows a higher fluorescence intensity than that absorbed by ssDNA. Actually, in the measured results, the structure of dsDNA showed the higher fluorescence intensity. Thus, the method is applicable to DNA high sensitivity sensing.

The manufacturing technique of the metal structure of the present invention is the technique with extremely high versatility, and is capable of providing minute integrated structures of not only gold but also silver, platinum and the like. Further, its shape is not limited to the shape of a block, and it is possible to provide minute integrated structures formed of various kinds and types of shapes such as, for example, the shape of a disk, nano-rod-shape, nano-wire-shape and the like.

Thus, the present invention provides excellent metal structures (sensing devices), sensing apparatus and sensing method in development of fine metals structures having the plasmon optical response function and multiphoton absorption function that is the important technique in development of current optical devices and development of highly sensitive sensors.

The present application is based on Japanese Patent Application No. 2005-080579, filed on Mar. 18, 2005, the entire content of which is expressly incorporated by reference herein.

INDUSTRIAL APPLICABILITY

The sensing device, sensing apparatus and sensing method according to the present invention are capable of implementing efficient multiphoton absorption and fluorescent sensing based on the multiphoton absorption by localized plasmon enhancing effect. The sensing device, sensing apparatus and sensing method according to the present invention have the remarkable effect capable of providing multiphoton absorption and fluorescent sensing based on the multiphoton absorption with the spectral sensitivity function, and are useful as the sensing device, sensing apparatus and sensing method having the multiphoton absorption/florescence enhancement function and the wavelength selective function thereof. Particularly, the metal structure (sensing device) capable of controlling the plasmon resonance absorption wavelength according to the present invention is useful as an elemental technique for developing various kinds of optical devices and highly sensitive biosensors.

The invention claimed is:

1. A sensing device exhibiting plasmon resonance absorption, comprising on a substrate a plurality of fine metal particles having a uniform size and arranged in a fixed direction at regular intervals,
   wherein the plurality of fine metal particles each have four vertexes that have a same shape when seen from an upper side perpendicular to the substrate;
   the plurality of fine metal particles are arranged such that a distance between facing vertexes of the fine metal particles is 30 nanometers or less and a distance between facing side surfaces of the fine metal particles is greater than the distance between facing vertexes of diagonally positioned particles; and
   a variability in the size of the fine metal particles is 5 percent or less.

2. The sensing device according to claim 1, wherein a height of the plurality of fine metal particles is between 10 nanometers and 100 nanometers and a variability in the height is 10 percent or less.

3. The sensing device according to claim 1, wherein the substrate comprises a solid transparent substrate.

4. A sensing apparatus comprising:
   a sensing device exhibiting plasmon resonance absorption, comprising on a substrate a plurality of fine metal particles having a uniform size and arranged in a fixed direction at regular intervals, wherein
      the plurality of fine metal particles each have four vertexes that have a same shape when seen from an upper side perpendicular to the substrate,
      the plurality of fine metal particles are arranged such that a distance between facing vertexes of the fine metal particles is 30 nanometers or less and a distance between facing side surfaces of the fine metal particles is greater than the distance between facing vertexes of diagonally positioned particles, and
      a variability of the size of the fine metal particles is 5 percent or less;
   an excitation light irradiating section that irradiates an excitation light that makes a sensing-target substance adsorbed to the sensing device emit fluorescence to the sensing device; and
   a fluorescence intensity measuring section that measures an intensity of the fluorescence of the sensing-target substance.

5. The sensing apparatus according to claim 4, further comprising a sensing-target substance analyzing section that analyzes the intensity of fluorescence to calculate quantitatively an amount of the sensing-target substance adsorbed to the sensing device.

6. The sensing apparatus according to claim 4, wherein a height of the plurality of fine metal particles is between 10 nanometers and 100 nanometers and a variability in the height is 10 percent or less.

7. A sensing method comprising the steps of:
   irradiating an excitation light that makes a sensing-target substance adsorbed to a sensing device emit fluorescence to the sensing device, wherein the sensing device comprises on a substrate a plurality of fine metal particles having a uniform size and arranged in a fixed direction at regular intervals, wherein the plurality of fine metal particles each have four vertexes that have a same shape when seen from an upper side perpendicular to the substrate, the plurality of fine metal particles arranged such that a distance between facing vertexes of the fine metal particles is 30 nanometers or less and a distance between facing side surfaces of the fine metal particles is greater than the distance between facing vertexes of diagonally positioned particles, and a variability in the size is 5 percent or less;
   measuring an intensity of the fluorescence of the sensing-target substance.

8. The sensing device according to claim 1, wherein the minimum distance is 10 nanometers or less.

\* \* \* \* \*